(12) United States Patent
Sablone et al.

(10) Patent No.: US 10,470,939 B2
(45) Date of Patent: *Nov. 12, 2019

(54) PANT-TYPE DIAPER AND CORRESPONDING MANUFACTURING PROCESS AND APPARATUS

(71) Applicant: Fameccanica.Data S.p.A., Sambuceto di San Giovanni Teatino (IT)

(72) Inventors: Gabriele Sablone, Montesilvano (IT); Paolo Pasqualoni, San Giovanni Teatino (IT)

(73) Assignee: Fameccanica.Data S.p.A., Sambuceto di San Giovanni Teatino, Chieti (IT)

( * ) Notice: Subject to any disclaimer, the term of this patent is extended or adjusted under 35 U.S.C. 154(b) by 849 days.

This patent is subject to a terminal disclaimer.

(21) Appl. No.: 14/971,454

(22) Filed: Dec. 16, 2015

(65) Prior Publication Data

US 2016/0100991 A1    Apr. 14, 2016

Related U.S. Application Data

(60) Division of application No. 13/350,464, filed on Jan. 13, 2012, now Pat. No. 9,248,056, which is a
(Continued)

(51) Int. Cl.
*A61F 13/15* (2006.01)
*A61F 13/56* (2006.01)
(Continued)

(52) U.S. Cl.
CPC .. *A61F 13/15756* (2013.01); *A61F 13/15723* (2013.01); *A61F 13/15747* (2013.01);
(Continued)

(58) Field of Classification Search
CPC .......... A61F 13/15756; A61F 13/49058; A61F 13/622; A61F 13/15723
See application file for complete search history.

(56) References Cited

U.S. PATENT DOCUMENTS

| 3,870,292 A | 3/1975 | Bradley |
| 3,994,486 A | 11/1976 | Nystrand |

(Continued)

FOREIGN PATENT DOCUMENTS

| CA | 2332075 A1 | 7/2001 |
| EP | 0983760 | 3/2000 |

(Continued)

OTHER PUBLICATIONS

Disclosure under 37 CFR 1.56 for U.S. Appl. No. 13/350,464, filed May 24, 2012.

(Continued)

*Primary Examiner* — Mark A Osele
*Assistant Examiner* — Christopher C Caillouet
(74) *Attorney, Agent, or Firm* — Eversheds Sutherland (US) LLP

(57) ABSTRACT

A prefastened, refastenable pant and methods and apparatus for preparing the same are provided. The pant comprises a chassis having a leading and trailing edge, and first and second lateral edges, wherein the chassis is folded-over along a transverse fold line orthogonal to the first and second lateral edges of the chassis. A pair of first side panels may be attached to the chassis proximal one of the leading and trailing edge of the chassis, each comprising a first fastening component. A pair of second side panels may be attached to the chassis proximal another of the leading and trailing edge of the chassis, each comprising a second fastening component. Each of the pair of first side panels is detachably secured to the chassis and the first fastening components and second fastening components are refastenably engaged between the first and second lateral edges of the chassis.

19 Claims, 12 Drawing Sheets

Related U.S. Application Data continuation-in-part of application No. 13/299,145, filed on Nov. 17, 2011, now abandoned, which is a continuation-in-part of application No. 13/006,159, filed on Jan. 13, 2011, now abandoned.

(51) Int. Cl.
*A61F 13/62* (2006.01)
*A61F 13/49* (2006.01)
*A61F 13/496* (2006.01)

(52) U.S. Cl.
CPC ...... *A61F 13/15764* (2013.01); *A61F 13/496* (2013.01); *A61F 13/49058* (2013.01); *A61F 13/565* (2013.01); *A61F 13/5655* (2013.01); *A61F 13/62* (2013.01); *A61F 13/622* (2013.01); *A61F 2013/5677* (2013.01)

(56) References Cited

U.S. PATENT DOCUMENTS

| | | |
|---|---|---|
| 4,022,456 A | 5/1977 | Hooper et al. |
| 4,055,859 A | 11/1977 | Green et al. |
| 4,081,301 A | 3/1978 | Buell |
| 4,610,680 A | 9/1986 | LaFleur |
| 4,650,173 A | 3/1987 | Johnson et al. |
| 4,699,622 A | 10/1987 | Toussant et al. |
| 4,738,440 A | 4/1988 | Weir |
| 4,761,937 A | 8/1988 | Francioni |
| 4,834,736 A | 5/1989 | Boland et al. |
| 4,834,738 A | 5/1989 | Kielpikowski et al. |
| 4,908,247 A | 3/1990 | Baird et al. |
| 4,938,753 A | 7/1990 | Van Gompel et al. |
| 4,940,464 A | 7/1990 | Van Gompel et al. |
| 5,046,272 A | 9/1991 | Vogt et al. |
| 5,087,253 A | 2/1992 | Cooper |
| 5,092,862 A | 3/1992 | Muckenfuhs et al. |
| 5,147,343 A | 9/1992 | Kellenberger |
| 5,156,902 A | 10/1992 | Pieper et al. |
| 5,213,645 A | 5/1993 | Nomura et al. |
| 5,259,902 A | 11/1993 | Muckenfuhs |
| 5,269,776 A | 12/1993 | Lancaster et al. |
| 5,286,543 A | 2/1994 | Ungpiyakul et al. |
| 5,383,872 A | 1/1995 | Roessler et al. |
| 5,435,802 A | 7/1995 | Kober |
| 5,476,053 A | 12/1995 | Brocklehurst |
| 5,496,298 A | 3/1996 | Kuepper et al. |
| 5,542,942 A | 8/1996 | Kline et al. |
| 5,556,360 A | 9/1996 | Kober et al. |
| 5,556,504 A | 9/1996 | Rajala et al. |
| 5,569,234 A | 10/1996 | Buell et al. |
| 5,601,542 A | 2/1997 | Melius et al. |
| 5,626,711 A | 5/1997 | Herrmann |
| 5,649,920 A | 7/1997 | Lavon et al. |
| 5,669,996 A | 9/1997 | Jessup |
| 5,702,551 A | 12/1997 | Huber et al. |
| 5,745,922 A | 5/1998 | Rajala et al. |
| 5,765,495 A | 6/1998 | Adamski, Jr. |
| 5,772,825 A | 6/1998 | Schmitz |
| 5,776,389 A | 7/1998 | Chaudhary |
| 5,779,831 A | 7/1998 | Schmitz |
| 5,788,805 A | 8/1998 | Herrmann |
| 5,795,433 A | 8/1998 | Niedemeyer |
| 5,797,831 A | 8/1998 | Roberts et al. |
| 5,803,448 A | 9/1998 | Stiel et al. |
| 5,836,932 A | 11/1998 | Buell et al. |
| 5,865,135 A | 2/1999 | Price et al. |
| 5,904,802 A | 5/1999 | Niedemeyer |
| 5,915,319 A | 6/1999 | Price et al. |
| 5,916,203 A | 6/1999 | Brandon et al. |
| 5,919,334 A | 7/1999 | Niedermeyer |
| 5,938,652 A | 8/1999 | Sauer |
| 5,940,887 A | 8/1999 | Rajala et al. |
| 5,980,439 A | 11/1999 | Johnson et al. |
| 6,022,431 A | 2/2000 | Bienke et al. |
| 6,022,432 A | 2/2000 | Elsberg et al. |
| 6,027,440 A | 2/2000 | Roth |
| 6,036,805 A | 3/2000 | McNichols |
| 6,098,203 A | 8/2000 | Rajala et al. |
| 6,113,717 A | 9/2000 | Vogt et al. |
| 6,210,388 B1 | 4/2001 | Widlund et al. |
| 6,213,991 B1 | 4/2001 | Kling et al. |
| 6,248,098 B1 | 6/2001 | Sayama |
| 6,260,211 B1 | 7/2001 | Rajala et al. |
| 6,264,639 B1 | 7/2001 | Sauer |
| 6,264,643 B1 | 7/2001 | Toyoda |
| 6,307,119 B1 | 10/2001 | Cammarota et al. |
| 6,328,725 B2 | 12/2001 | Fernors |
| 6,395,115 B1 | 5/2002 | Popp et al. |
| 6,402,731 B1 | 6/2002 | Suprise et al. |
| 6,409,858 B1 | 6/2002 | Popp et al. |
| 6,432,243 B1 | 8/2002 | Popp et al. |
| 6,432,248 B1 | 8/2002 | Popp et al. |
| 6,447,497 B1 | 9/2002 | Olson |
| 6,447,628 B1 | 9/2002 | Couillard et al. |
| 6,454,751 B1 | 9/2002 | Olson |
| 6,454,752 B1 | 9/2002 | Huang et al. |
| 6,461,343 B1 | 10/2002 | Schaefer et al. |
| 6,461,344 B1 | 10/2002 | Widlund et al. |
| 6,461,471 B1 | 10/2002 | Tharpe, Jr. et al. |
| 6,475,205 B2 | 11/2002 | Shimada et al. |
| 6,497,032 B2 | 12/2002 | Maxton et al. |
| 6,500,161 B1 | 12/2002 | Freiburger et al. |
| 6,513,221 B2 | 2/2003 | Vogt et al. |
| 6,514,187 B2 | 2/2003 | Coenen et al. |
| 6,524,293 B1 | 2/2003 | Elsberg et al. |
| 6,531,015 B1 | 3/2003 | Gardner, Jr. |
| 6,562,167 B2 | 5/2003 | Coenen et al. |
| 6,565,691 B2 | 5/2003 | Tomsovic et al. |
| 6,575,953 B2 | 6/2003 | Olson |
| 6,579,275 B1 | 6/2003 | Pozniak et al. |
| 6,596,107 B2 | 7/2003 | Stopher |
| 6,596,113 B2 | 7/2003 | Csida et al. |
| 6,613,033 B1 | 9/2003 | Popp et al. |
| 6,635,135 B2 | 10/2003 | Kuen et al. |
| 6,645,190 B1 | 11/2003 | Olson et al. |
| 6,648,871 B2 | 11/2003 | Kusibojoska et al. |
| 6,652,696 B2* | 11/2003 | Kuen ............... A61F 13/15699 156/204 |
| 6,667,085 B1 | 12/2003 | McNichols |
| 6,669,618 B2 | 12/2003 | Reising et al. |
| 6,682,626 B2 | 1/2004 | Mlinar et al. |
| 6,702,798 B2 | 3/2004 | Christoffel et al. |
| 6,708,855 B2 | 3/2004 | Wilson et al. |
| 6,723,034 B2 | 4/2004 | Durrance et al. |
| 6,723,035 B2 | 4/2004 | Franklin et al. |
| 6,730,188 B2 | 5/2004 | Sanders |
| 6,743,321 B2 | 6/2004 | Guralski et al. |
| 6,752,796 B2 | 6/2004 | Karami |
| 6,761,711 B1 | 7/2004 | Fletcher et al. |
| 6,764,475 B1 | 7/2004 | Olson |
| 6,776,316 B2 | 8/2004 | Van Eperen et al. |
| 6,793,650 B2 | 9/2004 | Weber |
| 6,808,787 B2 | 10/2004 | Coenen et al. |
| 6,817,994 B2 | 11/2004 | Popp et al. |
| 6,821,370 B2 | 11/2004 | Tomsovic et al. |
| 6,846,374 B2 | 1/2005 | Popp et al. |
| 6,849,067 B2 | 2/2005 | Fletcher et al. |
| 6,854,624 B2 | 2/2005 | Vogt et al. |
| 6,872,267 B2 | 3/2005 | Popp et al. |
| 6,878,223 B2* | 4/2005 | Kuen ............... A61F 13/15699 156/204 |
| 6,885,451 B2 | 4/2005 | Vogt et al. |
| 6,888,143 B2 | 5/2005 | Vogt et al. |
| 6,893,388 B2 | 5/2005 | Reising et al. |
| 6,893,426 B1 | 5/2005 | Popp et al. |
| 6,915,829 B2 | 7/2005 | Popp et al. |
| 6,915,929 B2 | 7/2005 | Kauch et al. |
| 6,919,965 B2 | 7/2005 | Koele et al. |
| 6,923,798 B2 | 8/2005 | Hedén et al. |
| 6,976,521 B2 | 12/2005 | Mlinar et al. |
| 6,976,978 B2 | 12/2005 | Ruman et al. |
| 6,994,697 B2 | 2/2006 | Shimada et al. |
| 7,000,260 B2 | 2/2006 | Rajala et al. |

(56) References Cited

U.S. PATENT DOCUMENTS

| | | | |
|---|---|---|---|
| 7,039,997 B2 | 5/2006 | Vogt et al. |
| 7,069,970 B2 | 7/2006 | Tomsovic et al. |
| 7,077,834 B2 | 7/2006 | Bishop et al. |
| 7,123,765 B2 | 10/2006 | Carbone, II et al. |
| 7,132,031 B2 | 11/2006 | Ohiro et al. |
| 7,150,730 B2 | 12/2006 | Hasler et al. |
| 7,154,018 B2 | 12/2006 | Koenig et al. |
| 7,156,833 B2 | 1/2007 | Couture-Dorschner et al. |
| 7,156,939 B2 | 1/2007 | Vogt et al. |
| 7,175,584 B2 | 2/2007 | Maxton et al. |
| 7,195,586 B2 | 3/2007 | Yamamoto et al. |
| 7,198,622 B2 | 4/2007 | Dahlgren |
| 7,201,744 B2 | 4/2007 | Van Gompel et al. |
| 7,207,979 B2 | 4/2007 | Price et al. |
| 7,214,285 B2 | 5/2007 | Guenther et al. |
| 7,229,515 B2 | 6/2007 | Couillard et al. |
| 7,270,631 B2 | 9/2007 | Franklin et al. |
| 7,297,139 B2 | 11/2007 | Price et al. |
| 7,318,798 B2 | 1/2008 | Yamamoto et al. |
| 7,322,925 B2 | 1/2008 | Couillard et al. |
| 7,322,967 B2 | 1/2008 | Kondo |
| 7,322,968 B2 | 1/2008 | Shimoe |
| 7,335,150 B2 | 2/2008 | Coenen et al. |
| 7,387,148 B2 | 6/2008 | Vogt et al. |
| 7,390,373 B2 | 6/2008 | Karisson et al. |
| 7,407,468 B2 | 8/2008 | Reising et al. |
| 7,425,242 B2 | 9/2008 | Olsson et al. |
| 7,431,791 B2 | 10/2008 | Heller et al. |
| 7,435,245 B2 | 10/2008 | Wendelstorf et al. |
| 7,449,017 B2 | 11/2008 | Yoshida |
| 7,452,320 B2 | 11/2008 | Csida et al. |
| 7,455,665 B2 | 11/2008 | Wendelstorf et al. |
| 7,459,050 B2 | 12/2008 | Karlsson et al. |
| 7,524,313 B2 | 4/2009 | Kline et al. |
| 7,534,237 B2 | 5/2009 | Olson et al. |
| 7,578,812 B2 | 8/2009 | Datta et al. |
| 7,582,076 B2 | 9/2009 | Yoshioka et al. |
| 7,621,901 B2 | 11/2009 | Karami |
| 7,637,898 B2 | 12/2009 | Kuen et al. |
| 7,682,349 B2 | 3/2010 | Popp et al. |
| 7,695,464 B2 | 4/2010 | Fletcher et al. |
| 7,737,324 B2 | 6/2010 | LaVon et al. |
| 7,766,887 B2 | 8/2010 | Burns, Jr. et al. |
| 7,833,207 B2 | 11/2010 | Kenmochi et al. |
| 7,842,849 B2 | 11/2010 | Datta |
| 7,857,801 B2 | 12/2010 | Haman et al. |
| 7,892,219 B2 | 2/2011 | Ito et al. |
| 7,901,392 B2 | 3/2011 | Kline et al. |
| 7,955,244 B2 | 6/2011 | Burns, Jr. et al. |
| 8,043,273 B2 | 10/2011 | Van Gompel et al. |
| 8,043,274 B2 | 10/2011 | Mlinar et al. |
| 8,053,625 B2 | 11/2011 | Nhah et al. |
| 8,066,686 B2 | 11/2011 | Coomans |
| 8,353,891 B2 | 1/2013 | Hornung et al. |
| 9,248,056 B2 * | 2/2016 | Sablone .................. A61F 13/62 |
| 2003/0066609 A1 | 4/2003 | Calvert |
| 2003/0168614 A1 * | 9/2003 | Vogt ........................ A61F 13/15 |
| | | | 250/492.1 |
| 2003/0216706 A1 | 11/2003 | Olsson et al. |
| 2005/0177127 A1 | 8/2005 | Ashton et al. |
| 2005/0256489 A1 | 11/2005 | Sawyer et al. |
| 2005/0277905 A1 | 12/2005 | Pedersen et al. |
| 2007/0049890 A1 | 3/2007 | Popp et al. |
| 2007/0049897 A1 | 3/2007 | LaVon et al. |
| 2007/0113984 A1 | 5/2007 | Pasqualoni |
| 2007/0213678 A1 | 9/2007 | Thorson et al. |
| 2007/0287980 A1 | 12/2007 | Kline et al. |
| 2008/0195074 A1 | 8/2008 | Popp et al. |
| 2008/0249493 A1 | 10/2008 | Kobayashi et al. |
| 2009/0043275 A1 | 2/2009 | Perneborn |
| 2009/0198206 A1 | 8/2009 | Kline et al. |
| 2009/0254059 A1 | 10/2009 | Nilsson et al. |
| 2009/0277564 A1 | 11/2009 | Widlund et al. |
| 2010/0057029 A1 | 3/2010 | Popp et al. |
| 2010/0114048 A1 | 5/2010 | Bishop et al. |
| 2010/0121293 A1 | 5/2010 | Fletcher et al. |
| 2010/0191211 A1 | 7/2010 | Molander |
| 2010/0215908 A1 | 8/2010 | Kline et al. |
| 2010/0215913 A1 | 8/2010 | Kline et al. |
| 2010/0217217 A1 | 8/2010 | Kline et al. |
| 2010/0217219 A1 | 8/2010 | Kline et al. |
| 2010/0217220 A1 | 8/2010 | Kline et al. |
| 2010/0217221 A1 | 8/2010 | Kline et al. |
| 2010/0217222 A1 | 8/2010 | Kline et al. |
| 2010/0262110 A1 | 10/2010 | Lakso |
| 2010/0262112 A1 | 10/2010 | Bäck et al. |
| 2010/0298803 A1 | 11/2010 | Popp et al. |
| 2010/0305532 A1 | 12/2010 | Ashton et al. |
| 2011/0072561 A1 | 3/2011 | Kinoshita et al. |
| 2011/0082436 A1 | 4/2011 | Meetz et al. |
| 2011/0098668 A1 | 4/2011 | Thorson et al. |
| 2011/0106042 A1 | 5/2011 | Sablone et al. |
| 2011/0114245 A1 | 5/2011 | Nhan et al. |
| 2011/0125125 A1 | 5/2011 | Schneider et al. |

FOREIGN PATENT DOCUMENTS

| | | | |
|---|---|---|---|
| EP | 1772403 A1 | 4/2007 |
| EP | 1289465 B1 | 2/2008 |
| EP | 1289466 B1 | 2/2008 |
| EP | 1284700 B1 | 4/2008 |
| EP | 0755238 B2 | 5/2008 |
| GB | 2244422 | 12/1991 |
| GB | 2303045 A | 2/1997 |
| IT | 195581 B | 1/1983 |
| IT | PE92A000001 | 1/1992 |
| IT | PE2004A000001 | 2/2004 |
| JP | 7205943 | 8/1995 |
| JP | 9131364 | 5/1997 |
| WO | 93/17648 | 9/1993 |
| WO | 95/27462 A1 | 10/1995 |
| WO | 95/29657 | 11/1995 |
| WO | 96/21408 | 7/1996 |
| WO | 97/46197 A1 | 12/1997 |
| WO | 98/18421 | 5/1998 |
| WO | 00/37007 A1 | 6/2000 |
| WO | 01/91666 A2 | 12/2001 |
| WO | 2009/083788 A1 | 7/2009 |
| WO | 2010/008032 A1 | 1/2010 |

OTHER PUBLICATIONS

PCT International Search Report and Written Opinion dated Feb. 25, 2011 for PCT/IB2010/054797.

PCT International Search Report and Written Opinion dated May 2, 2012 for PCT/IB2012/000046.

U.S. Statutory Invention Registration N. H1674 to Ames et al., published Aug. 5, 1997.

* cited by examiner

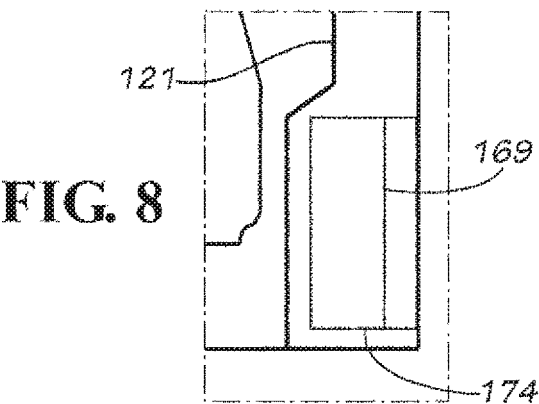

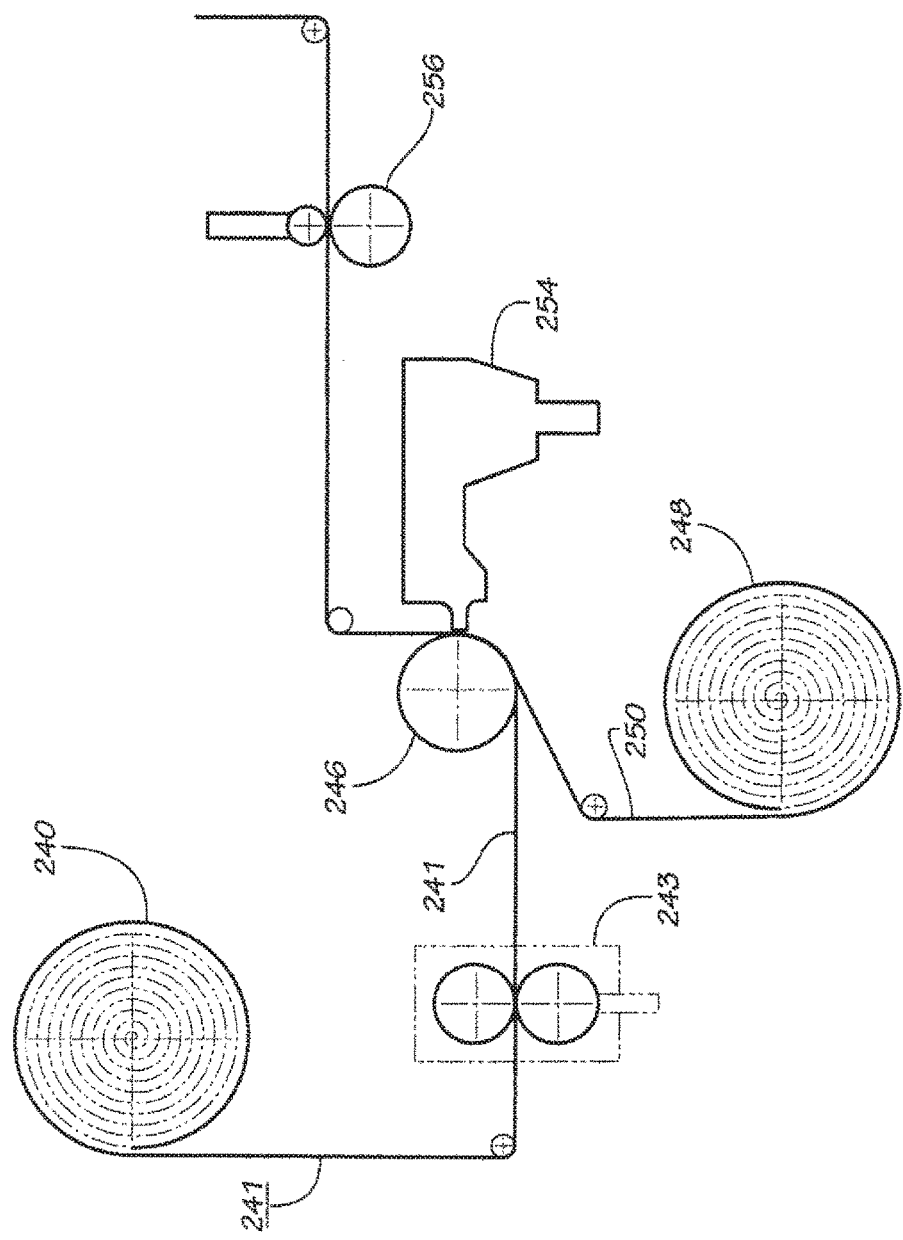

PANT-TYPE DIAPER AND CORRESPONDING MANUFACTURING PROCESS AND APPARATUS

CROSS REFERENCE TO RELATED APPLICATIONS

This application is a divisional of U.S. patent application Ser. No. 13/350,464, filed Jan. 13, 2012, which is a continuation-in-part of now abandoned U.S. patent application Ser. No. 13/299,145, filed Nov. 17, 2011, which is a continuation-in-part of now abandoned U.S. patent application Ser. No. 13/006,159, filed on Jan. 13, 2011, all of which are hereby incorporated herein in their entirety by reference.

BACKGROUND

This disclosure relates to absorbent sanitary products. More particularly, this disclosure relates to refastenable absorbent sanitary products that can be worn like pants.

Over the last few years, there has emerged interest in diapers of the type commonly referred to as "training pants". When such a product is taken out of the pack, it has already a conformation that substantially resembles that of the pair of pants. It is put on by sliding it over the legs of the user according to criteria basically similar to the ones adopted for putting on pants.

A training pant typically includes a central body or chassis that contains an absorbent core which is designed to absorb the body fluids evacuated by the wearer. Side panels extend laterally from the chassis so as to complete the pant-like configuration of the product. The side panels are provided with homologous distal edges designed to be connected (pre-fastened) to one another to form lateral closure regions. In the most recent products the pre-fastened closure regions are intended to be refastenable, thus permitting the product—which is sold in a pre-fastened, closed pant-like condition—to be selectively opened at either side in order to check e.g. whether the product is soiled.

Documents such as U.S. Pat. No. 6,761,711; 6,849,067; 6,645,190; or 7,534,237 are exemplary of arrangements of refastenable side closures.

Various patent documents such as U.S. Pat. No. 6,514,187; 7,322,925; 7,335,150; 7,387,148 or EP-A-1 289 465, EP-A-2 289 466, or EP-A-1 284 700 are exemplary of processes and apparatus which may be applied to manufacturing products with refastenable side closures.

Despite the effectiveness of the results obtained, the various arrangements considered in the foregoing have an intrinsic disadvantage in that the associated manufacturing processes and apparatus are inevitably complex, expensive and exposed to criticalities in terms of reliability.

It would therefore be desirable to provide a solution dispensing with one of more or all of these drawbacks while leading to product structure retaining the advantages discussed in the foregoing. The claims are an integral part of the disclosure of the invention as provided herein.

SUMMARY OF THE INVENTION

In one aspect, a method is provided for preparing a refastenable article. The method includes providing a refastenable training pant comprising a chassis having a leading edge, a trailing edge, and first and second lateral edges extending in a longitudinal direction between the leading edge and the trailing edge, the refastenable training pant comprising a first pair of side panels attached to the chassis proximal one of the leading edge and trailing edge of the chassis and a second pair of side panels attached to the chassis proximal another of the leading edge and the trailing edge of the chassis, wherein the first pair of side panels each comprise a first fastening component and the second pair of side panels each comprise a second fastening component; wherein the first pair of side panels are folded inwardly over the chassis such that the first fastening components lie between the first and second lateral edges of the chassis, and wherein the second pair of side panels are folded inwardly over the chassis such that the second fastening components lie between the first and second lateral edges of the chassis; and refastenably engaging at least a portion of the first fastening components and at least a portion of the second fastening components while the first fastening components and second fastening components lie between the first and second lateral edges of the chassis.

In another aspect, a method is provided for preparing a refastenable training pant. The method includes providing a topsheet for forming a portion of a pant chassis; applying a pair of first side panels to the topsheet, each of the pair of first side panels having a refastenable fastening element; folding each of the first side panels to form first folded portions; and detachably securing the first folded portion of each of the first side panels to the pant chassis.

In another aspect, a refastenable training pant is provided. The refastenable training pant includes a chassis having a leading edge, a trailing edge, and first and second lateral edges extending in a longitudinal direction between the leading edge and the trailing edge. The chassis is folded-over along a transverse fold line orthogonal to the first and second lateral edges. The training pant also includes a pair of first side panels attached to the chassis proximal one of the leading edge and the trailing edge of the chassis. Each of the pair of first side panels comprises a first fastening component. The training pant further includes a pair of second side panels attached to the chassis proximal another of the leading edge and the trailing edge of the chassis. Each of the pair of second side panels comprises a second fastening component. Each of the pair of first side panels is detachably secured to the chassis and the first fastening components and second fastening components are refastenably engaged between the first and second lateral edges of the chassis.

In yet another aspect, an apparatus is provided for preparing a refastenable training pant. The apparatus includes a first side panel attachment device adapted to attach a first side panel having a first refastenable fastening element to a pant chassis. The pant chassis has first and second lateral edges. The side panel attachment device is adapted to attach the first side panel to the pant chassis adjacent to the first lateral edge of the pant chassis. The apparatus further includes a first side panel folding device adapted to receive the first side panel and fold the first side panel in a direction substantially transverse to the first and second lateral edges of the pant chassis to form a first folded portion. When attached to the pant chassis, the first folded portion is folded inwardly over the pant chassis and extends between the first and second lateral edges of the pant chassis. The apparatus further includes a securing device that is adapted to detachably secure the first folded portion of the first side panel to the pant chassis.

In another aspect, an apparatus is provided for preparing a refastenable training pant. The pant assembly system is configured to prepare a refastenable training pant comprising a chassis having a leading edge, a trailing edge, and a first and a second lateral edge extending in a longitudinal direction between the leading edge and the trailing edge. The refastenable training pant includes a first pair of side panels attached to the chassis proximal one of the leading edge and the trailing edge of the chassis and a second pair of side panels attached to the chassis proximal to another of the leading edge and the trailing edge of the chassis, wherein the first pair of side panels each comprise a first fastening component and the second pair of side panels each comprise a second fastening component. The first pair of side panels is folded inwardly over the chassis such that the first fastening components lie between the first and second lateral edges of the chassis, and the second pair of side panels are folded inwardly over the chassis such that the second fastening components lie between the first and second lateral edges of the chassis. The apparatus includes a pant transport device adapted to transport the refastenable training pant in a machine direction while the first and second fastening components lie between the first and second lateral edges of the chassis in an unfastened state. The apparatus further includes a fastening station adapted to refastenably engage at least a portion of the first fastening components and at least a portion of the second fastening components while the first fastening components and second fastening components lie between the first and second lateral edges of the chassis.

BRIEF DESCRIPTION OF THE SEVERAL DRAWING VIEWS

The invention will now be described, by way of example only, with reference to the annexed representations, wherein:

FIG. 8 is a partial plan view of a refastenable article in a flattened-out configuration, showing details of the folding of a back side panel in accordance with one or more embodiments of the present disclosure.

FIG. 9 is a partial schematic cross-section showing a refastenable article in accordance with one or more embodiments of the present disclosure.

FIG. 13 is a schematic example of a method for producing back side panels in accordance with one or more embodiments of the present disclosure.

DETAILED DESCRIPTION

Figure 1:
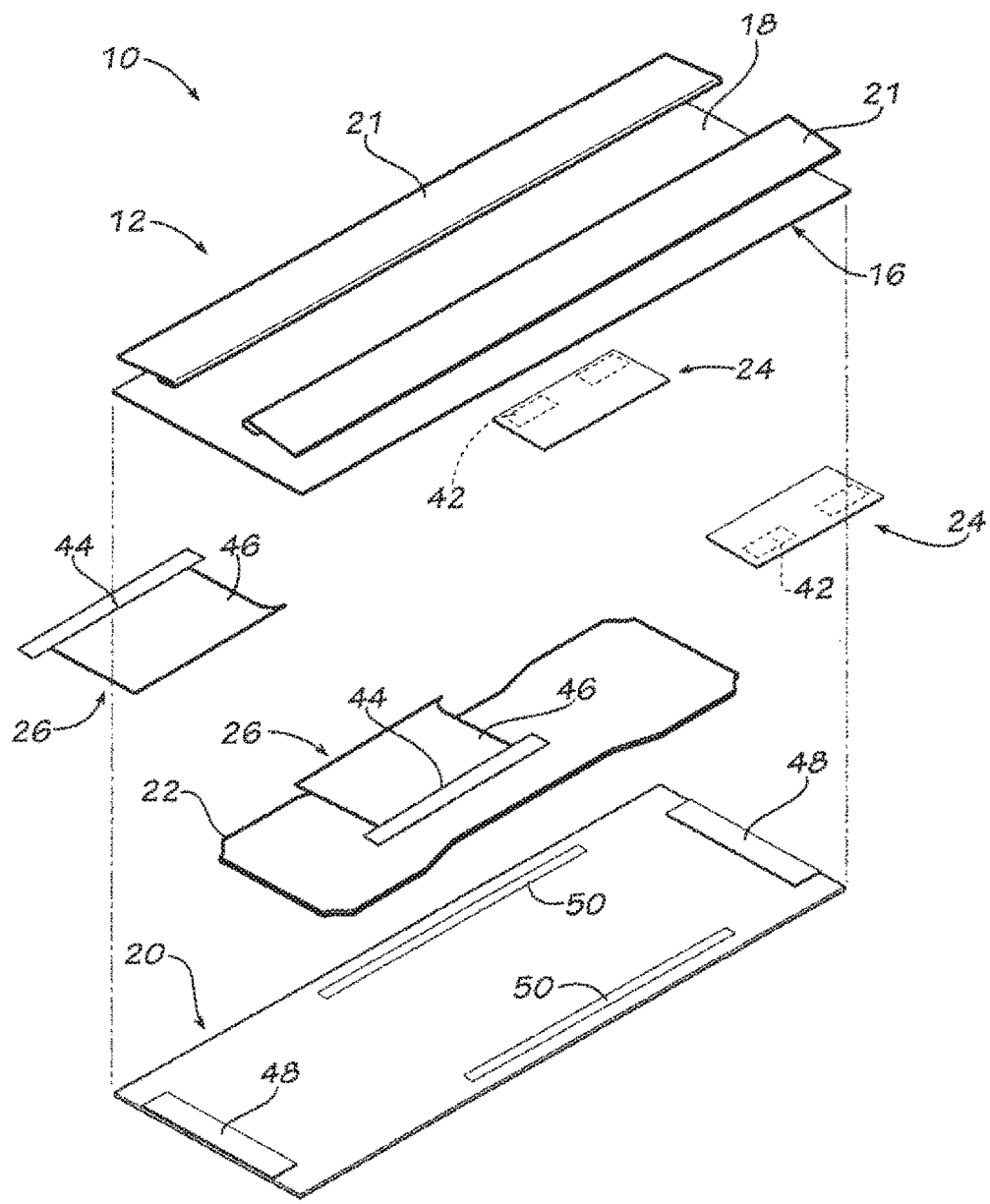
FIG. 1 is an exploded perspective view of a refastenable article according to one or more embodiments of the present disclosure.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms "first," "second," "third," and "fourth" as used herein in reference to side panels, breakable bonds, fastening components, edges and the like is not intended to refer to any specific order that the components are formed or added to a pant chassis during the manufacturing process or otherwise limit the claims to any specific embodiment illustrated or described herein. Instead, the terms are merely intended to clarify that a referenced component is different than a similar mentioned component.

Refastenable Training Pants

Refastenable training pants are provided in a prefastened and folded configuration. The refastenable training pant includes a chassis having a leading edge, a trailing edge, and first and second lateral edges extending in a longitudinal direction between the leading edge and the trailing edge. The chassis is folded-over along a transverse fold line orthogonal to the first and second lateral edges. The refastenable training pant further includes a pair of first side panels attached to the chassis proximal one of the leading edge and the trailing edge of the chassis. The refastenable training pant also includes a pair of second side panels attached to the chassis proximal another of the leading edge and the trailing edge of the chassis. Each of the first and second side panels includes fastening components. The fastening components of the first and second side panels are refastenably engaged between the first and second lateral edges of the chassis. In some embodiments, the fastening components may comprise, for example, hook and loop fasteners.

The refastenable training pant also includes detachably secured first side panels. As used herein, the term "detachably secured" (or "detachably securing") means a temporary securement and/or attachment to the refastenable training pant, such that detaching the securement does not result in destruction of the components of the refastenable training pant or unfastening of the refastenable fastening components. In some embodiments, components may be detachably secured with a breakable bond between components. For example, the refastenable training pant may include a first breakable bond between each of the pair of first side panels and the chassis. In other embodiments, each of the pair of first side panels may be detachably secured in a respective pocket that is formed between a barrier leg cuff and the topsheet The term "breakable bond" as used herein refers to a temporary connection made between components of the refastenable training pant that are weaker than the bonds that are employed to fix the side panels to the chassis such that when the refastenable article is opened and the breakable bonds are broken the side panels are not destroyed and the refastenable fastening components are not unfastened. The breakable bonds may be, for example, an adhesive bond, an ultrasonic bond, or a thermal bond.

In an exemplary embodiment, each of the first side panels may be folded inwardly into the chassis such that a first folded portion of each of the first side panels lies between the first and second lateral edges of the chassis. In such an embodiment, the refastenable training pant may include a first breakable bond between the first folded portion of each of the pair of first side panels and the chassis between the first and second lateral edges of the chassis. For example, each of the first breakable bonds may be located between the respective first side panel and the chassis. The first breakable bond may have a sufficiently weak bond strength such that the first breakable bond may be broken when the training pant is opened to be worn.

In an exemplary embodiment, each of the second side panels may be folded inwardly into the chassis such that a second folded portion of each of the second side panels lies between the first and second lateral edges of the chassis. In such an embodiment, the refastenable training pant may further include a second breakable bond between the second folded portion of each of the pair of second side panels and the chassis between the first and second lateral edges of the chassis. Each of the pair of second side panels may be folded outwardly over the second folded portion of each side panels such that a third folded portion of each of the second pair of side panels lies between the first and second lateral edges of the chassis. In such an embodiment, the refastenable training pant may further include a third breakable bond between the third folded portion of each of the second pair of side panels and the chassis between the first and second lateral edges of the chassis.

In some embodiments, the third breakable bond may be formed between at least a first tabbed portion of the third folded portion and the chassis, where the at least a first tabbed portion extends from a trailing edge or a leading edge of a distal region of the third folded portion. In still other embodiments, the refastenable training pant may further include a fourth breakable bond between the third folded portion of each of the second pair of side panels and the chassis between the first and second lateral edges of the chassis. In some embodiments, the fourth breakable bond may be formed between a second tabbed portion of the third folded portion and the chassis, where the second tabbed portion extends from another of the trailing edge or a leading edge of a distal region of the third folded portion.

In still other embodiments, the third breakable bond may be formed between the third folded portion and the second folded portion of each of the second side panels.

In some embodiments, each of the second side panels may be folded inwardly into the chassis such that a second folded portion of each of the second side panels lies between the first and second lateral edges of the chassis. Each of the pair of second side panels then may be folded outwardly over the second folded portion of each side panels such that a third folded portion of each of the second pair of side panels lies between the first and second lateral edges of the chassis. The second folded portion, in this embodiment, may not be bonded to the third folded portion. In such an embodiment, the refastenable training pant may further include a third breakable bond between the third folded portion of each of the second pair of side panels and the chassis between the first and second lateral edges of the chassis. In some embodiments, the third breakable bond may be formed between at least a first tabbed portion of the third folded portion and the chassis, where the at least a first tabbed portion extends from a trailing edge or a leading edge of a distal region of the third folded portion. In still other embodiments, the refastenable training pant may further include a fourth breakable bond between the third folded portion of each of the second pair of side panels and the chassis between the first and second lateral edges of the chassis. In some embodiments, the fourth breakable bond may be formed between a second tabbed portion of the third folded portion and the chassis, where the second tabbed portion extends from another of the trailing edge or a leading edge of a distal region of the third folded portion.

In other embodiments, the second folded portion may be bonded to the third folded portion. In still other embodiments, a third breakable bond may be formed between the third folded portion of each of the second side panels and the respective second folded portion of each of the second side panels between the first and second lateral edges of the chassis.

In still other embodiments, the refastenable training pant may not comprise a breakable bond. For example, each of the first side panels may be folded and then at least partially inserted into respective pockets located adjacent to each of the first and second lateral edges of the chassis. The respective pockets may detachably secure the folded portions of the first side panels to the chassis such that when the training pant is opened to be worn, the folded portions of the first side panels are released from the respective pockets.

In an exemplary embodiment, each of the first side panels may be folded inwardly over the chassis such that a first folded portion of each of the first side panels lies between the first and second lateral edges of the chassis. In such an embodiment, each of the first folded portions of the pair of first side panels may be folded and then at least partially inserted into respective pockets located adjacent to each of the first and second lateral edges of the chassis.

In an exemplary embodiment, each of the second side panels may be folded inwardly over the chassis such that a second folded portion of each of the second side panels lies between the first and second lateral edges of the chassis. Each of the pair of second side panels may be folded outwardly over the second folded portion of each of the side panels such that a third folded portion of each of the second pair of side panels lies between the first and second lateral edges of the chassis. In such an embodiment, each of the second folded portions and third folded portions of the pair of second side panels may be folded and then at least partially inserted into respective pockets located adjacent to each of the first and second lateral edges of the chassis.

In an exemplary embodiment, the refastenable training pant may include first side panels that include a fastening component comprising hook material. In some embodiments, the fastening component comprising hook material may be located on the non-body side of the first side panels. In some embodiments, the refastenable training pant may include second side panels that include a fastening component comprising loop material. In some embodiments, the fastening component comprising loop material may be located on the body side of the second side panels. In still other embodiments, the second side panels may comprise a loop material such that the second side panels may themselves serve as the fastening components.

As used herein, the term "non-body side" of a side panel means the portion of a side panel that is not facing towards the body of a person wearing the refastenable training pant, or, in other words, is facing outward from the body. As used herein, the term "body side" of a side panel means the portion of a side panel that faces towards the body of a person wearing the refastenable training pant, or, in other words, faces inwardly toward the body of the wearer.

The training pant chassis may comprise an at least partially fluid-permeable topsheet, a fluid-impermeable backsheet, and an absorbent core sandwiched between the topsheet and the backsheet. The topsheet and the backsheet may be bonded together along an outer perimeter. In such embodiments, each of the pair of first side panels may be permanently affixed to one of the first and second lateral edges of the chassis, and the first folded portions may be folded inwardly with respect to the outer perimeter over the topsheet so that the folded portion of each of the pair of first side panels may also be detachably secured to the chassis. In some embodiments, each folded portion of the pair of first side panels may be detachably secured to the chassis by a first breakable bond. In another embodiment, each folded portion of the pair of first side panels may be detachably secured to the chassis by at least partially inserting the folded portions into respective pockets.

In some embodiments, each of the pair of second side panels may be permanently affixed to one of the first and second lateral edges of the chassis, and each of the pair of second side panels is folded along a substantially S-shaped configuration and has second folded portions folded inwardly with respect to the outer perimeter of the chassis, over the topsheet along respective second fold lines and third folded portions folded along third fold lines over the respective second folded portions.

Each of the folded portions of the second side panels may also be detachably secured to the chassis. Each of the second folded portions may optionally be connected to the topsheet by a second breakable bond and each of the third folded portions may be connected to the chassis and/or topsheet by at least a third breakable bond. In still other embodiments, each of the third folded portions may instead be connected to the second folded portions by a third breakable bond. In yet other embodiments, each of the folded portions of the pair of second side panels may be detachably secured to the chassis by at least partially inserting the folded portions into respective pockets.

The first and/or second side panels may have respective lower edges shaped to anatomically conform to the legs of a wearer. In some embodiments, the first and second side panels may both be made of an elasticized material. In other embodiments, only one of the first and second side panels may be made of an elasticized material. Accordingly, in some embodiments, the first or second side panels may be made of a non-elasticized material. In some embodiments, one of the first and second fastening components may comprise a loop element formed by surface loops of the material constituting the corresponding side panel. In some embodiments, the first side panels may be substantially longer in a direction transverse to the first and second lateral edges than the second side panels. In another embodiment, the second side panels may be substantially longer in a direction transverse to the first and second lateral edges than the first side panels. In yet another embodiment, the first and second side panels may be substantially the same length in a direction transverse to the first and second lateral edges.

An exemplary embodiment of a refastenable training pant is illustrated in FIGS. 1-5. In FIGS. 1-5 the reference number 10 indicates a refastenable article 10 wearable as a pant-like garment. The refastenable article 10 comprises a chassis 12. The chassis is defined by the two opposite lateral edges 14 and the front waist edge 41 and back waist edge 43.

With reference to FIG. 1, the chassis 12 includes a topsheet 16 at least partially made of a fluid-permeable material, having an inner surface 18 which in use contacts the skin of the wearer.

The topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. For example, the material may be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant may be applied by any conventional means, such as spraying, printing, brush coating or the like. The surfactant may be applied to the entire topsheet 16 or may be selectively applied to particular sections of the topsheet, such as the medial section along the longitudinal center line.

A suitable liquid permeable topsheet 16 is a nonwoven bicomponent web having a basis weight of about 27 gsm (grams per square meter). The nonwoven bicomponent may be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber.

The topsheet 16 may include barrier leg cuffs 21 applied on the inner surface 18 which are configured to provide a barrier to the transverse flow of body exudates. A flap elastic member (FIG. 2) may be operatively joined with each leg cuff 21 in any suitable manner as is well known in the art. The leg cuffs 21 define a pair of edges, each assuming an upright configuration in at least the crotch region 29 of the refastenable article 10 to form a seal against the wearer's body. The elastic leg cuffs 21 may be located along the transversely opposed side edges, i.e., the lateral edges 14 of the chassis 12, and may extend longitudinally along the entire length of the absorbent chassis or may only extend partially along the length of the chassis 12. Suitable constructions and arrangements for the elastic leg cuffs 21 are generally well known to those skilled in the art and are described in U.S. Pat. No. 4,704,116 issued Nov. 3, 1987 to Enloe.

The chassis 12 may include a fluid-impermeable backsheet 20. The backsheet 20 may be a single layer of liquid impermeable material, but desirably comprises a multi-layered laminate structure in which at least one of the layers is liquid impermeable. For instance, the backsheet 20 may include a liquid permeable outer layer and a liquid impermeable inner layer that are suitably joined together by laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgwater, N.J. U.S.A.

The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable backsheet 20 is made. While it is not a necessity for outer layer to be liquid permeable, it is desired that it provides a relatively cloth-like texture to the wearer.

The inner layer of the backsheet 20 may be both liquid and vapor impermeable, or it may be liquid impermeable and vapor permeable. The inner layer may be manufactured from a thin plastic film, although other flexible liquid impermeable materials may also be used. The inner layer, or the liquid impermeable backsheet 20 when a single layer, prevents waste material from wetting articles, such as bedsheets and clothing, as well as the wearer and caregiver. A suitable liquid impermeable film for use as a liquid impermeable inner layer, or a single layer liquid impermeable backsheet 20, is a 0.02 millimeter polyethylene film commercially available from Huntsman Packaging of Newport News, Va. U.S.A. If the backsheet 20 is a single layer of material, it may be embossed and/or matte finished to provide a more cloth-like appearance. As earlier mentioned, the liquid impermeable material may permit vapors to escape from the interior of the disposable absorbent article, while still preventing liquids from passing through the backsheet 20. A suitable "breathable" material may be composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO8044 polyolefin film commercially available from 3M Company, Minneapolis, Minn. U.S.A.

The chassis 12 may also include an absorbent core 22. The absorbent core 22 may be positioned between the backsheet 20 and the topsheet 16, which components may be joined together by any suitable means such as adhesives, ultrasonic bonds, thermal bonds, or the like. The absorbent core 22 may be any structure which is generally compressible, conformable, non-irritating to the wearer's skin, and capable of absorbing and retaining liquids and certain body wastes. The absorbent core 22 may be manufactured in a wide variety of sizes and shapes, and from a wide variety of liquid absorbent materials commonly used in the art. For example, the absorbent core 22 may suitably comprise a matrix of hydrophilic fibers, such as a web of cellulosic fluff, mixed with particles of a high-absorbency material commonly known as superabsorbent material. In a particular embodiment, the absorbent core 22 may comprise a matrix of cellulosic fluff, such as wood pulp fluff, and superabsorbent hydrogel-forming particles. The wood pulp fluff may be exchanged with synthetic, polymeric, meltblown fibers or short cut homofil bicomponent synthetic fibers and natural fibers. The superabsorbent particles may be substantially homogeneously mixed with the hydrophilic fibers or can be non-uniformly mixed. The fluff and superabsorbent particles may also be selectively placed into desired zones of the absorbent core 22 to better contain and absorb body exudates. The concentration of the superabsorbent particles may also vary through the thickness of the absorbent core 22. Alternatively, the absorbent core 22 may comprise a laminate of fibrous webs and superabsorbent material or other suitable means of maintaining a superabsorbent material in a localized area.

Suitable superabsorbent materials may be selected from natural, synthetic, and modified natural polymers and materials. The superabsorbent materials may be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent core 22 which can be rectangular or any other desired shape may comprise a blend of wood pulp fluff and superabsorbent material. One preferred type of pulp is identified with the trade designation CR1654, available from U. S. Alliance, Childersburg, Ala. U.S.A., and is a bleached, highly absorbent sulphate wood pulp containing primarily soft wood fibers and about 16 percent hardwood fibers. The superabsorbent material may be present in the absorbent core 22 in an amount of from 0 to about 90 weight percent based on total weight of the absorbent assembly. The absorbent core 22 suitably has a density within the range of about 0.10 to about 0.35 grams per cubic centimeter. The absorbent core 22 may or may not be wrapped or encompassed by a suitable tissue wrap that may help maintain the integrity and/or shape of the absorbent assembly.

The chassis 12 may also incorporate other materials that are designed primarily to receive, temporarily store, and/or transport liquid along the mutually facing surface with absorbent core 22, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

The topsheet 16 and the backsheet 20 may be bonded together along an outer perimeter of the chassis 12.

Figure 2:
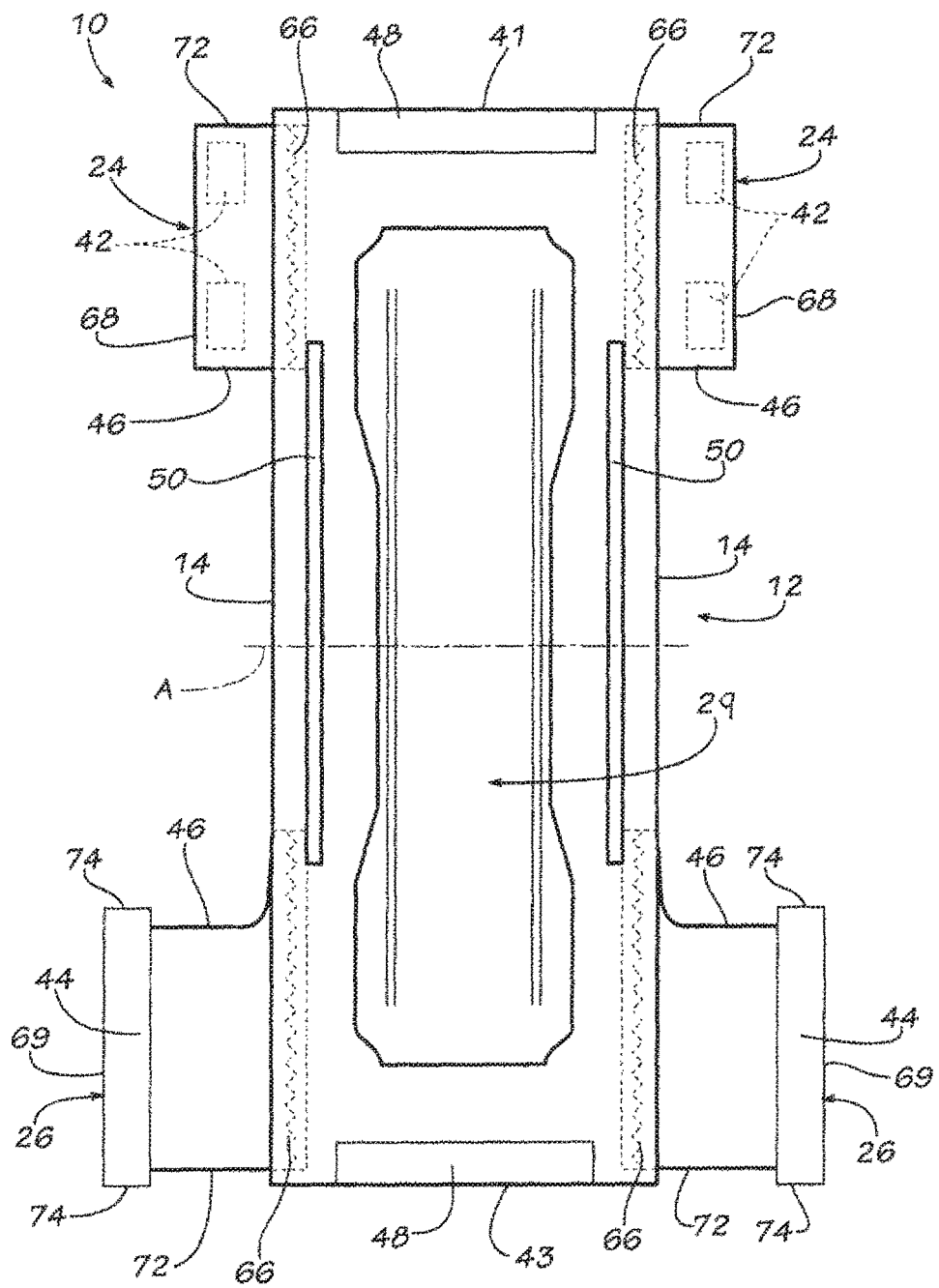
FIG. 2 is a plan view of a refastenable article in a flattened-out configuration in accordance with one or more embodiments of the present disclosure.

In some embodiments, refastenable article 10 may be manufactured and sold with the chassis 12 folded-over along a central transversal fold line, indicated A in FIG. 2, transversal to the lateral edges 14 of the chassis.

Figure 3:
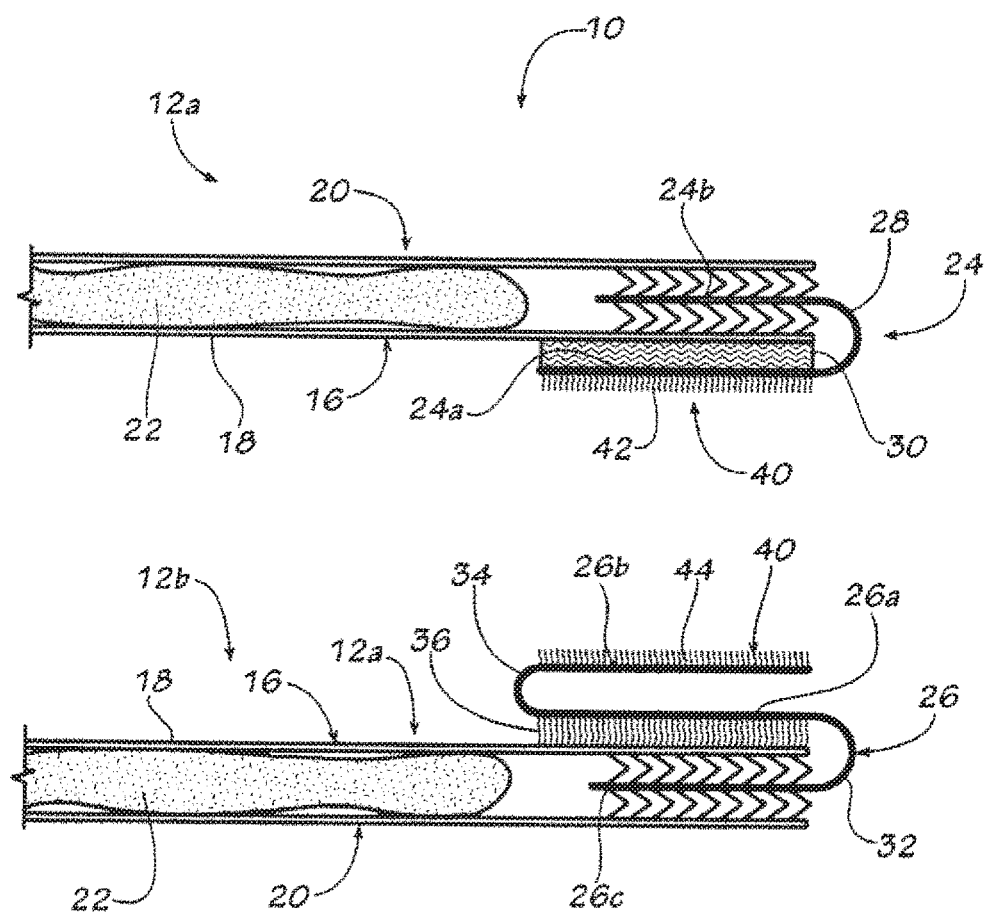
FIG. 3 is a partial schematic cross-section showing a refastenable article in accordance with one or more embodiments of the present disclosure.

As shown in FIG. 3, in an exemplary configuration in which the refastenable article 10 may be manufactured and sold the chassis 12 has two folded portions 12a, 12b, with respective portions of the inner surface 18 of the topsheet 16 facing each other.

The refastenable article 10 may comprise two front side panels 24 and two back side panels 26 fixed to respective lateral edges 14 of the chassis 12. The terms "front" and "back" refer to the condition in which the refastenable article 10 is worn by the user. It should be noted that the orientation of the front side panels 24 and back side panels 26 may be reversed in some embodiments such that the back side panels 26 are worn in the front and the front side panels 24 are worn in the back.

These transversely opposed front side panels 24 and transversely opposed back side panels 26 can be permanently bonded along attachment lines 66 to the chassis 12 of the respective front and back waist regions. More particularly, as shown in FIGS. 2 and 3, the front side panels 24 may be permanently bonded to and extend transversely beyond the side edges 14 of the chassis 12 in the front waist region, and the back side panels 26 may be permanently bonded to and extend transversely beyond the side edges of the chassis 12 in the back waist region. The side panels 24 and 26 may be attached using attachment means known to those skilled in the art such as adhesive, thermal or ultrasonic bonding or the like. The front and back side panels 24 and 26 may be releasably attached to one another as illustrated by the fastening system 40.

The illustrated side panels 24 and 26 each define a respective distal edge 68 and 69 that is spaced from the attachment line 66, a leg end edge 46 disposed toward the longitudinal center of the training pant 10, and a waist end edge 72 disposed toward a longitudinal end of the chassis. The leg end edge 46 and waist end edge 72 extend from the lateral edges 14 of the chassis 12 to the distal edges 68 and 69. In the back waist region, the leg end edges 46 may be curved and/or angled relative to the transverse axis A to provide greater coverage toward the back of the pant as compared to the front of the pant. The waist end edges 72 may be parallel to the transverse axis A. The waist end edges 72 of the front side panels 24 form part of the front waist edge 41 of the absorbent refastenable article 10, and the waist end edges 72 of the back side panels 26 form part of the back waist edge 43 of the refastenable article 10.

Each of the side panels 24 and 26 may include one or more individual, distinct pieces of material. In particular embodiments, for example, each side panel 24 and 26 may include first and second side panel portions that are joined at a seam, or can include a single piece of material.

The side panels 24 and 26 may comprise an elastic material capable of stretching in a direction generally parallel to the transverse axis A of the training pant 10. Suitable elastic materials are described in the following documents: EP 1 982 823 B1 and WO 2009/133508 A1.

With reference to FIG. 3, in the configuration in which the refastenable article 10 may be manufactured and sold the front side panels 24 have respective first folded portions 24a folded along respective first fold lines 28 inwardly with respect to the outer perimeter of the chassis 12 over the inner surface 18 of the topsheet 16. The first folded portions 24a may be detachably secured to the inner surface 18 of the topsheet 16, such as by respective first breakable bonds 30. The front side panels 24 may have respective fixing portions 24b which are fixed, e.g. by bonding, between the lateral edges of the topsheet 16 and backsheet 20.

The back side panels 26 may be folded according to a substantially S-shaped configuration and may have respective second folded portions 26a folded along respective second fold lines 32 inwardly with respect to the outer perimeter of the chassis 12 over the inner surface 18 of the topsheet 16. The back side panels 26 may also have respective third folded portions 26b folded along third fold lines 34 over the respective second folded portions 26a. The back side panels 26 may have respective fixing portions 26c which are fixed, e.g. by bonding, between the lateral edges of the topsheet 16 and backsheet 20.

Figure 4:
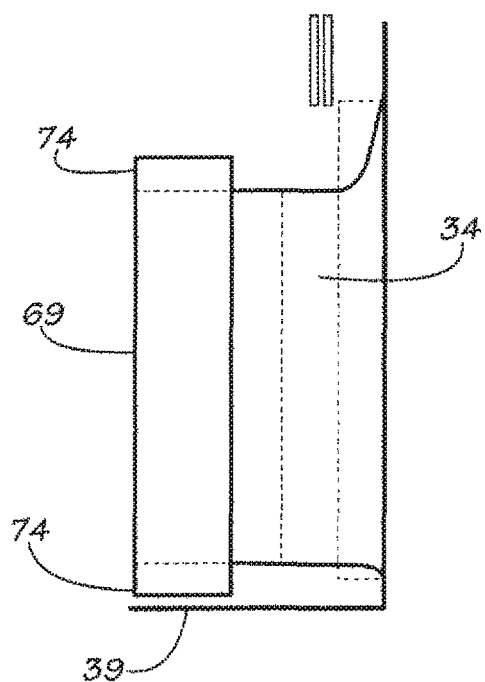
FIG. 4 is a partial plan view of a refastenable article in a flattened-out configuration, showing details of a second breakable bond between the second folded portion and a second side panel in accordance with embodiments of the present disclosure.

FIG. 4 shows details of the second breakable bond 36 that may be formed between the second folded portions 26a and the topsheet 16. As depicted, the second folded portions 26a of the back side panels 26 may be folded inwardly with respect to the outer perimeter of the chassis 12 over the inner surface 18. A second breakable bond 36 may then formed between the second folded portions 26a and the topsheet 16.

Figure 5:
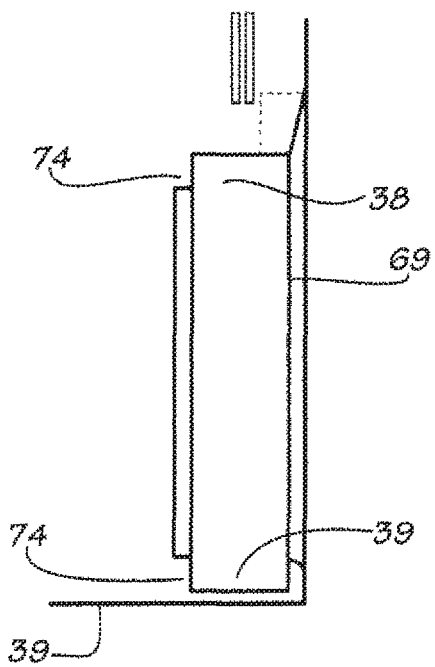
FIG. 5 is a partial plan view of a refastenable article in a flattened-out configuration, showing details of a third and a fourth breakable bond between a first tabbed portion and a second tabbed portion, respectively, and the chassis in accordance with embodiments of the present disclosure.

FIG. 5 shows details of the third breakable bond 38 and fourth breakable bond 39. As depicted, the third folded portions 26b of the back side panels 26 may be folded outwardly with respect to the outer perimeter of the chassis 12 over the inner surface 18. A third and a fourth breakable bond 38, 39 may then be formed between the second folded portions 26b and the topsheet 16. The third and fourth breakable bonds 38, 39 may be formed between the first and second tabbed portions 74 that extend from the leading edge and trailing edge of a distal region of the back side panels 26 and the topsheet 16.

In some embodiments, a second breakable bond 36 may not be formed. In such an embodiment, each of the pair of second side panels may be folded outwardly over the second folded portion 26a of each side panels such that a third folded portion 26b of each of the second pair of side panels lies between the first and second lateral edges of the chassis. In such an embodiment, the refastenable training pant may further include a third breakable bond 38 between the third folded portion 26b of each of the second pair of side panels and the chassis between the first and second lateral edges of the chassis. In some embodiments, the third breakable bond 38 may be formed between at least a first tabbed portion 74 of the third folded portion and the chassis, where the at least a first tabbed portion 74 extends from a trailing edge or a leading edge of a distal region of the third folded portion 26b. In still other embodiments, the refastenable training pant may further include a fourth breakable bond 39 between the third folded portion 26b of each of the second pair of side panels and the chassis between the first and second lateral edges of the chassis. In some embodiments, the fourth breakable bond 39 may be formed between a second tabbed portion 74 of the third folded portion 26b and the chassis, where the second tabbed portion 74 extends from another of the trailing edge or a leading edge of a distal region of the third folded portion 26b.

In some embodiments, the third breakable bond 38 may be formed between a first tabbed portion 74 of the third folded portion 26b of each of the second pair of side panels and the topsheet 16, and the fourth breakable bond 39 may be formed between a second tabbed portion 74 of the third folded portion 26b of each of the second pair of side panels and the topsheet 16. In some embodiments, the first tabbed portion 74 extends from one of a trailing edge or a leading edge of a distal region of the third folded portion 26b and the second tabbed portion 74 extends from another of the trailing edge and leading edge of the distal region of the third folded portion 26b. The back side panels 26 have respective fixing portions 26c which are fixed, e.g. by bonding, between the lateral edges of the topsheet 16 and backsheet 20.

In still other embodiments, a third breakable bond 38 may be formed between the third folded portion 26b of each of the second side panels and the respective second folded portion 26a of each of the second side panels between the first and second lateral edges of the chassis.

The first folded portions 24a of the front side panels 24 and the third folded portions 26b of the back side panels 26 have respective mutually facing surfaces. The refastenable article 10 may include two fastening components that form refastenable closures 40. Each fastening component may comprise a single fastening element or multiple fastening elements. The fastening components may comprise any refastenable fasteners suitable for absorbent articles, such as adhesive fasteners, cohesive fasteners, mechanical fasteners, or the like. In some embodiments, the side panel material itself may comprise the fastening component.

In particular embodiments the fastening components may comprise mechanical fastening elements for improved performance. Suitable mechanical fastening elements may be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density, and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

In one embodiment the refastenable article 10 may include a refastenable fastening system 40 comprising two refastenable closures, for example, complementary hook and loop fastening elements 42, 44 releasably engaged to each other. The hook and loop fastening elements 42, 44 may be fixed to the respective mutually facing surfaces of the first folded portions 24a and third folded portions 26b. The hook elements of the fastening system 40 may be provided either on the front side panels 24 or on the back side panels 26. In one embodiment the loop elements of the fastening system 40 may be constituted by surface loops of the material constituting the corresponding side panels 24 or 26.

It will be appreciated that, especially in FIG. 3, the relative proportions of parts and elements have been deliberately altered for ease of understanding. Also, in FIG. 3 the hook and loop fastening elements 42, 44 are shown separate (i.e. away) from each other. This is again done for ease of understanding, being otherwise understood that in the refastenable article 10 as finally produced, packaged, and sold, the hook and loop fastening elements 42, 44 of the fastening system 40 are engaged with each other to provide a closed condition of the refastenable article.

The first, second, third, and fourth breakable bonds 30, 36, 38, 39 may be formed by a layer of a so called "technical" or "green" glue or by a light bonding with thermal or ultrasonic bonding or the like. Suitable laminate adhesives, which may be applied continuously or intermittently as beads, a spray, parallel swirls, or the like, may be the AL11 obtained from Savarè I. C. of Milano, Italy. The temporary breakable bonds 30, 36, 38, 39 have the purpose of keeping the folded portions 24a, 26a, 26b detachably secured to the respective inner surfaces 18 of the topsheet 16 in order to avoid that the bent portions 24a, 26a, 26b undesirably "flap" outwardly with respect to the chassis 12 during the manufacturing process. The first, second, third, and fourth breakable bonds 30, 36, 38, 39 are designed to break when the refastenable article 10 is opened up to be worn. In some embodiments, the temporary breakable bonds 30, 36, 38, 39 may offer a peak resistance to breaking during the unfolding process of at least 25 N.

Figure 10:
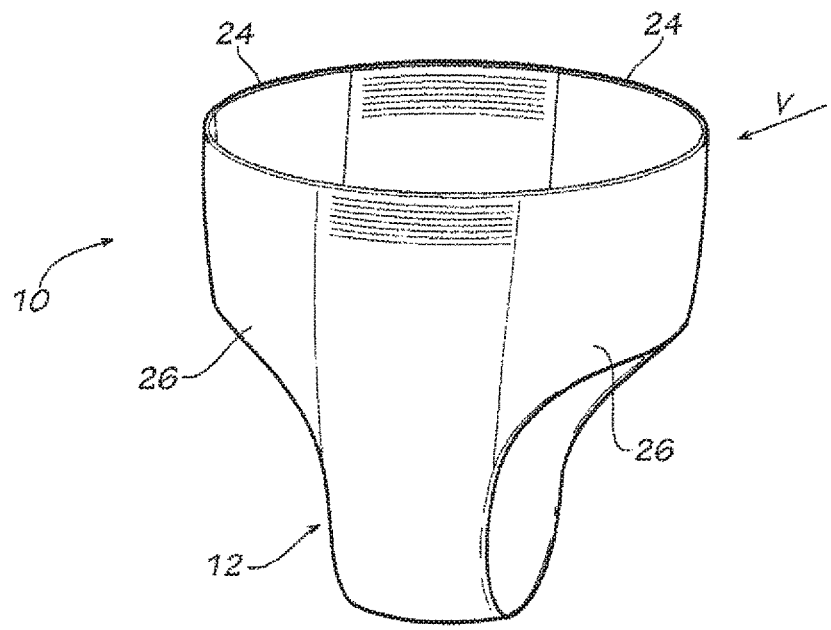
FIG. 10 is a perspective view of the refastenable article depicted in FIGS. 1-2 and 6-7 in a configuration of use in accordance with one or more embodiments of the present disclosure.
Figure 11:
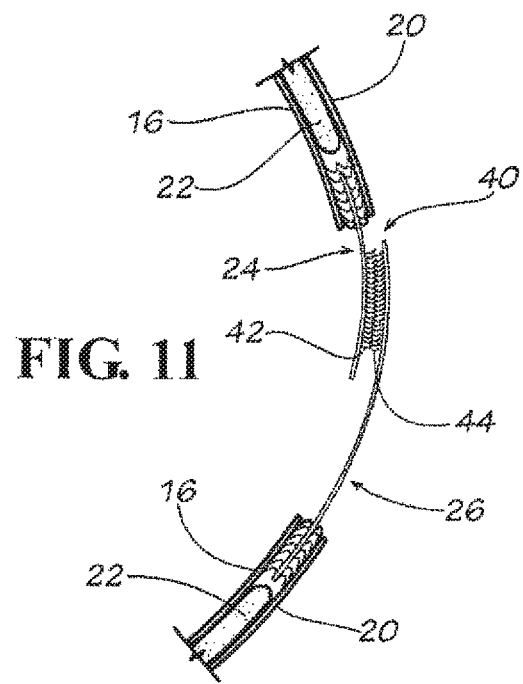
FIG. 11 is an enlarged detail of the part indicated by the arrow V in FIG. 10 in accordance with one or more embodiments of the present disclosure.

FIG. 10 shows the condition in which the refastenable article 10 may be opened so as to break the breakable bonds 30, 36, 38, 39. In this condition the folded portions 24a, 26a, 26b, after they are released from the detachable securement, may extend laterally outwardly from the chassis 12 at each of the opposite edges 14 to define respective portions of a waist line of the refastenable article 10. The detail of FIG. 11 shows the connection between one front side panel 24 and the corresponding back side panel 26 after release from the temporary bonds.

Referring to FIGS. 1 and 2, in an embodiment the back side panels 26 may have respective leg end edges 46 shaped to anatomically conform to the legs of the wearer. In some embodiments, the back side panels 26 may have a first tabbed portion 74, where the first tabbed portion 74 may be extending from one of a trailing edge and a leading edge of the distal region of the back side panels 26. In some embodiments, the back side panels 26 may have two tabbed portions 74, with a first tabbed portion 74 extending from one of a trailing edge and a leading edge of the distal region of the back side panel 26 and a second tabbed portion 74 extending from another of a trailing edge and a leading edge of the distal region of the back side panel 26.

In an embodiment, either the front side panels 24 or the back side panels 26 may be made of elasticized material. Both the front side panels 24 and the back side panels 26 may be made of elasticized material.

In an embodiment the refastenable article 10 may include two elastic waist members 48 extending on two opposite waist portions of the chassis 12 respectively between the two front side panels 24 and between the two back side panels 26. In other embodiments, the two elastic waist members 48 may not extend the entire distance between the two front side panels 24 and between the two back side panels 26. In still other embodiments, the refastenable article 10 may include two or more elastic waist members 48 extending between the two front side panels 24 and between the two back side panels 26.

In an embodiment, the chassis 12 may further include two elastic leg members 50 extending parallel to the opposite lateral edges 14 to provide a close fit of the refastenable article 10 around the wearer's legs. In other embodiments, the chassis 12 may include two or more elastic leg members 50 to provide a close fit of refastenable article 10 around the wearer's legs.

The elastic waist members 48 and the elastic leg members 50 may be formed of any suitable elastic material. As is well known to those skilled in the art, suitable elastic materials include sheets, strands or ribbons of natural rubber, synthetic rubber, or thermoplastic elastomeric polymers. The elastic materials may be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the elastic leg members 50 comprise a plurality of dry-spun coalesced multifilament spandex elastomeric threads sold under the trade name LYCRA and available from INVISTA, INVISTA Building, 4123 East 37th Street North, Wichita, Kans. 67220 U.S.A.

Another exemplary embodiment of a refastenable training pant is illustrated in FIGS. 6-9. In FIGS. 6-9 the reference number 100 indicates a refastenable article 100 wearable as a pant-like garment. The refastenable article 100 comprises a chassis 112. The chassis 112 is defined by the two opposite lateral edges 114 and the front waist edge 141 and back waist edge 143.

Figure 6:
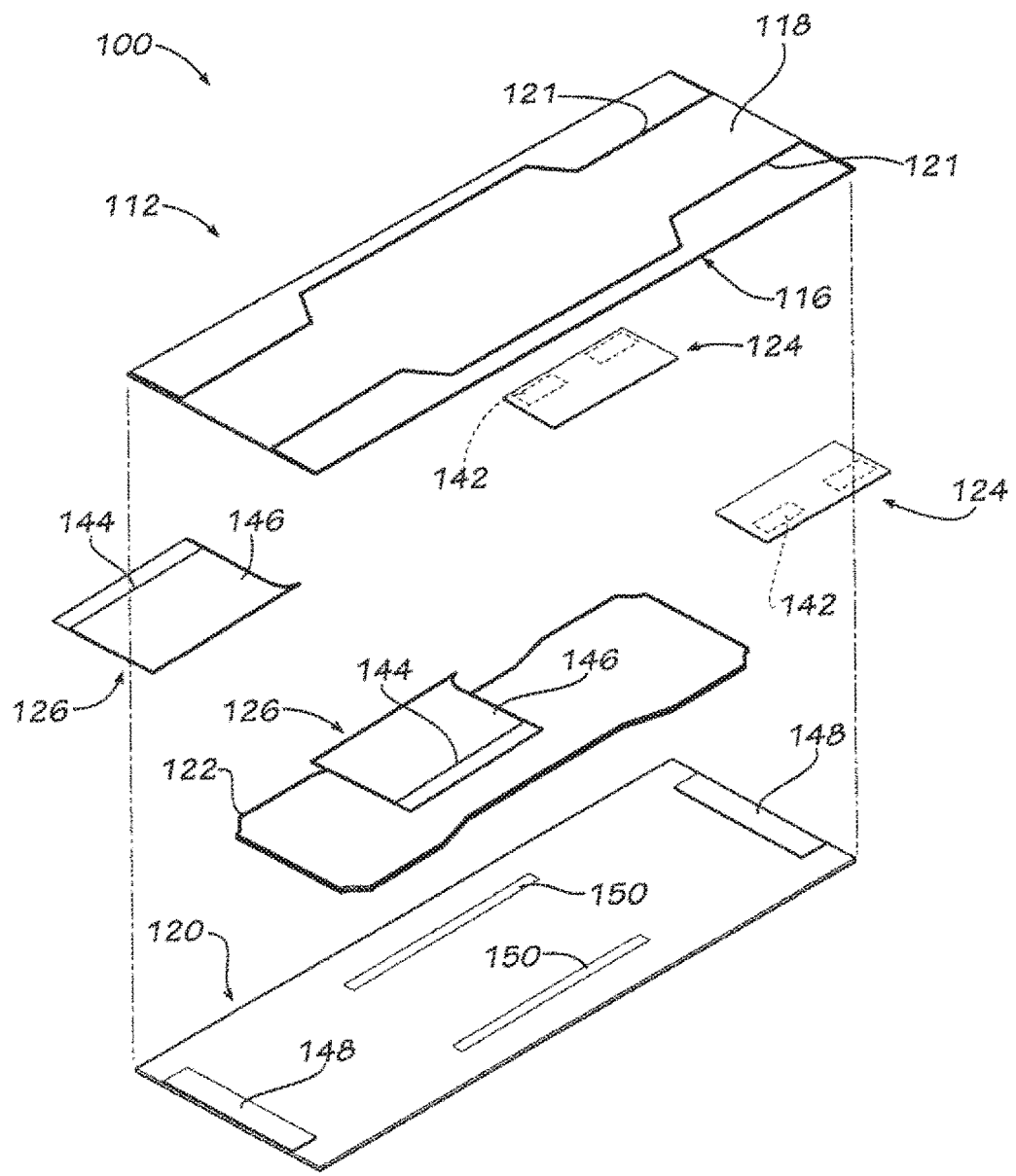
FIG. 6 is an exploded perspective view of a refastenable article according to one or more embodiments of the present disclosure.

With reference to FIG. 6, the chassis 112 may include a topsheet 116 at least partially made of a fluid-permeable material, having an inner surface 118 which in use contacts the skin of the wearer.

The topsheet may be composed of a meltblown or spun-bonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. The surfactant may be applied to the entire topsheet 116 or may be selectively applied to particular sections of the topsheet, such as the medial section along the longitudinal center line.

Figure 7:
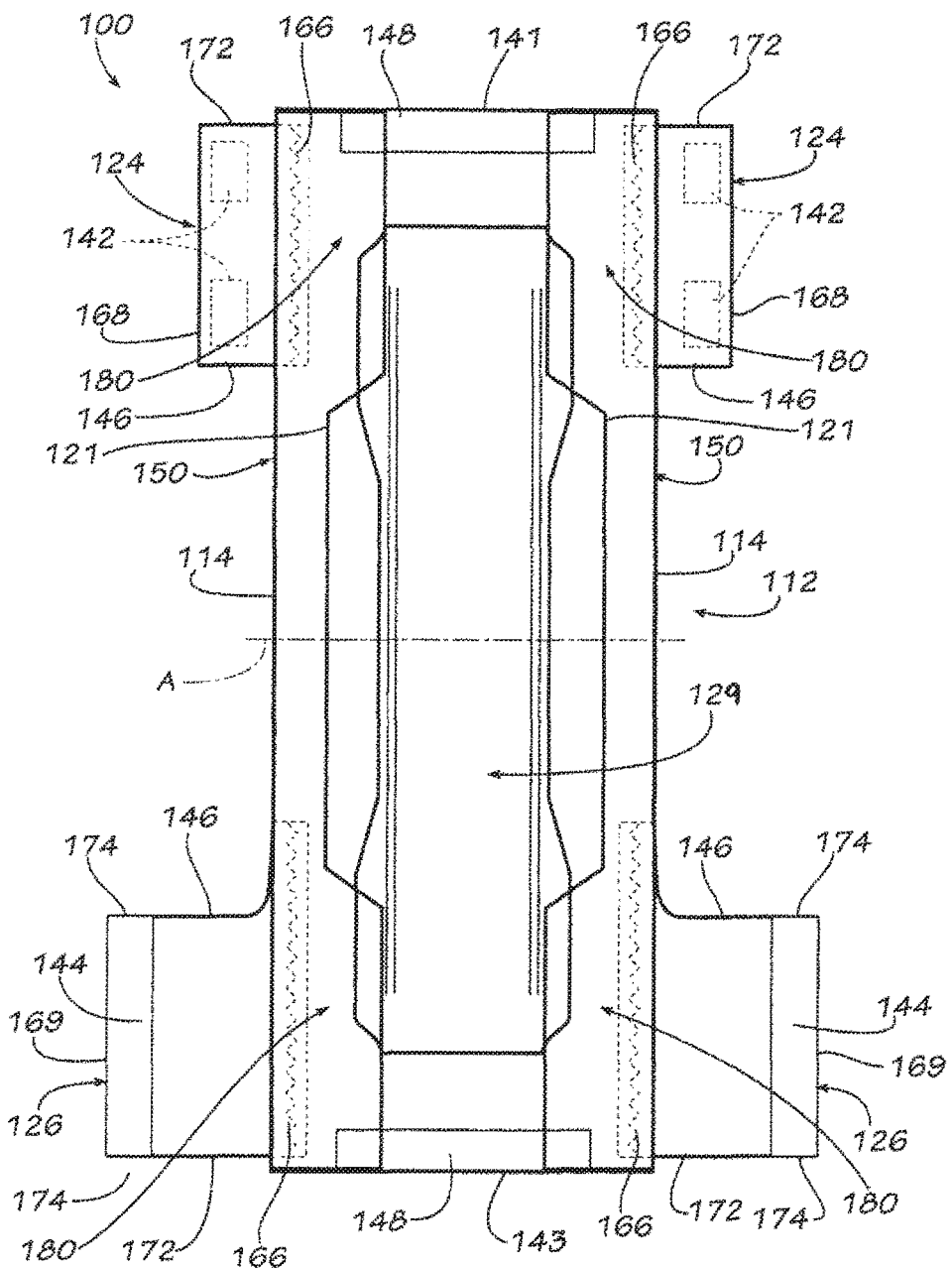
FIG. 7 is a plan view of a refastenable article in a flattened-out configuration in accordance with one or more embodiments of the present disclosure.

The topsheet 116 may include barrier leg cuffs 121 applied on the inner surface 118 which are configured to provide a barrier to the transverse flow of body exudates. The leg cuffs 121 define a pair of edge regions, each assuming an upright configuration in at least the crotch region 129 of the refastenable article 110 to form a seal against the wearer's body. The elastic leg cuffs 121 may be located along the transversely opposed side edges, i.e., the lateral edges 114 of the chassis 112, and may extend along the length of the chassis 112. As illustrated in FIG. 7, the leg cuffs 121 may be configured to provide four pockets 180 at the corners of the chassis 112. The pockets 180 may be formed between the inner surface 118 of the topsheet 116 and the leg cuffs 121.

The chassis 112 may include a fluid-impermeable backsheet 120. The backsheet 120 may be a single layer of liquid impermeable material, but may comprise a multi-layered laminate structure in which at least one of the layers may be liquid impermeable.

The inner layer of the backsheet 120 may be both liquid and vapor impermeable, or it may be liquid impermeable and vapor permeable. The inner layer may be manufactured from a thin plastic film, although other flexible liquid impermeable materials may also be used. The inner layer, or the liquid impermeable backsheet 120 when a single layer, prevents waste material from wetting articles, such as bedsheets and clothing, as well as the wearer and caregiver.

The chassis 112 may also include an absorbent core 122. The absorbent core 122 may be positioned between the backsheet 120 and the topsheet 116, which components may be joined together by any suitable means such as adhesives, ultrasonic bonds, thermal bonds, or the like. The absorbent core 122 may be any structure which is generally compressible, conformable, non-irritating to the wearer's skin, and capable of absorbing and retaining liquids and certain body wastes. The absorbent core 122 may be manufactured in a wide variety of sizes and shapes, and from a wide variety of liquid absorbent materials commonly used in the art.

The chassis 112 may also incorporate other materials that are designed primarily to receive, temporarily store, and/or transport liquid along the mutually facing surface with absorbent core 122, thereby maximizing the absorbent capacity of the absorbent assembly.

The topsheet 116 and the backsheet 120 may be bonded together along an outer perimeter of the chassis 112.

The transversely opposed front side panels 124 and transversely opposed back side panels 126 may be permanently bonded along attachment lines 166 to the chassis 112 of the respective front and back waist regions. More particularly, as shown in FIGS. 6 and 7, the front side panels 124 may be permanently bonded to and extend transversely beyond the side edges 114 of the chassis 112 in the front waist region, and the back side panels 126 may be permanently bonded to and extend transversely beyond the side edges of the chassis 112 in the back waist region. The side panels 124 and 126 may be attached using attachment means known to those skilled in the art such as adhesive, thermal or ultrasonic bonding or the like. The front and back side panels 124 and 126 may be releasably attached to one another as illustrated by the fastening system 140.

The illustrated side panels 124 and 126 each define a respective distal edge 168 and 169 that is spaced from the attachment line 166, a leg end edge 146 disposed toward the longitudinal center of the training pant 100, and a waist end edge 172 disposed toward a longitudinal end of the chassis. The leg end edge 146 and waist end edge 172 extend from the lateral edges 114 of the chassis 112 to the distal edges 168 and 169. In the back waist region, the leg end edges 146 may be curved and/or angled relative to the transverse axis A to provide greater coverage toward the back of the pant as compared to the front of the pant. The waist end edges 172 may be parallel to the transverse axis A. The waist end edges 172 of the front side panels 124 form part of the front waist edge 141 of the refastenable article 100, and the waist end edges 172 of the back side panels 126 form part of the back waist edge 143 of the refastenable article 100.

Each of the side panels 124 and 126 may include one or more individual, distinct pieces of material. In particular embodiments, for example, each side panel 124 and 126 may include first and second side panel portions that are joined at a seam, or can include a single piece of material.

The side panels 124 and 126 may comprise an elastic material capable of stretching in a direction generally parallel to the transverse axis A of the training pant 100. In some embodiments, the side panels 124 and 126 may all comprise an elastic material. In other embodiments, only side panels 124 may comprise an elastic material. In still other embodiments, only side panels 126 may comprise an elastic material.

In embodiments, the refastenable article 100 may be manufactured and sold with the chassis 112 folded-over along a central transversal fold line, indicated A in FIG. 7, transversal to the lateral edges 114.

As shown in FIG. 9, in an exemplary configuration in which the refastenable article 100 may be manufactured and sold the chassis 112 has two folded portions 112a, 112b, with respective portions of the inner surface 118 of the topsheet 116 facing each other.

The refastenable article 100 may comprise two front side panels 124 and two back side panels 126 fixed to respective lateral edges 114 of the chassis 112. These transversely opposed front side panels 124 and transversely opposed back side panels 126 may be permanently bonded along attachment lines 166 to the chassis 112 of the respective front and back waist regions. More particularly, as shown in FIG. 7, the front side panels 124 may be permanently bonded to and extend transversely beyond the side edges 114 of the chassis 112 in the front waist region, and the back side panels 126 may be permanently bonded to and extend transversely beyond the side edges of the chassis 112 in the back waist region. The front side panels 124 may have respective fixing portions 124b which are fixed, e.g. by bonding, between the lateral edges of the topsheet 116 and backsheet 120. The side panels 124 and 126 may be attached using attachment means known to those skilled in the art such as adhesive, thermal or ultrasonic bonding or the like. The front and back side panels 124 and 126 may be releasably attached to one another as illustrated by the fastening system 140.

With reference to FIG. 9, in the configuration in which the refastenable article 100 may be manufactured and sold the front side panels 124 may have respective first folded portions 124a folded along respective first fold lines 128 inwardly with respect to the outer perimeter of the chassis 112 over the inner surface 118 of the topsheet 116. The first folded portions 124a may be detachably secured to the inner surface 118 of the topsheet 116 by inserting at least a portion of the first folded portions 124a of the front side panels 124 into a pocket 180 formed between the inner surface 118 of the topsheet 116 and leg cuffs 121.

The back side panels 126 may be folded according to a substantially S-shaped configuration and have respective second folded portions 126a folded along respective second fold lines 132 inwardly with respect to the outer perimeter of the chassis 112 over the inner surface 118 of the topsheet 116. The back side panels 126 may also have respective third folded portions 126b folded along third fold lines 134 over the respective second folded portions 126a. The back side panels 126 have respective fixing portions 126c which are fixed, e.g. by bonding, between the lateral edges of the topsheet 116 and backsheet 120.

FIG. 8 shows details of the folding of the back side panels 126. As depicted, the second folded portions 126a of the back side panels 126 may be folded inwardly with respect to the outer perimeter of the chassis 112 over the inner surface 118. As depicted, the third folded portions 126b of the back side panels 126 may be folded outwardly with respect to the outer perimeter of the chassis 112 over the inner surface 118. As illustrated in FIG. 8, leg cuffs 121 may be configured to accommodate the folded back side panels 126 such that the folded back side panels 126 may be detachably secured in a pocket 180 that is formed between the inner surface 118 of the topsheet 116 and the leg cuffs 121.

The first folded portions 124a of the front side panels 124 and the third folded portions 126b of the back side panels 126 may have respective mutually facing surfaces. The refastenable article 100 may include two fastening components that form refastenable closures 140. Each fastening component may comprise a single fastening element or multiple fastening elements. The fastening components may comprise any refastenable fasteners suitable for absorbent articles, such as adhesive fasteners, cohesive fasteners, mechanical fasteners, or the like. In some embodiments, the side panel material itself may comprise the fastening component.

The refastenable article 100 may be opened so as to release the side panels 124 and 126 from their respective pockets 180. In this condition the folded portions 124a, 126a, and 126b, after they are released from the detachable securement, extend laterally outwardly from the chassis 12 at each of the opposite edges 114 to define respective portions of a waist line of the refastenable article 110. The detail of FIG. 10 shows refastenable article 10, which is analogous to refastenable article 100 for this illustration, that opens into a similar training pant product. The detail of FIG. 11, showing refastenable article 10, also by analogy, shows the details of refastenable article 100, with the connection between one front side panel 124 and the corresponding back side panel 126 after release from the respective pockets 180.

Methods of Manufacturing Refastenable Training Pants

Methods of preparing a refastenable article are also disclosed. In some embodiments, the methods include providing a refastenable training pant comprising a chassis having a leading edge, a trailing edge, and a first and a second lateral edge extending in a longitudinal direction between the leading edge and the trailing edge. The refastenable training pant may include a first pair of side panels attached to the chassis proximal one of the leading edge and the trailing edge of the chassis and a second pair of side panels attached to the chassis proximal another of the leading edge and the trailing edge of the chassis. The first pair of side panels each comprises a first fastening component and the second pair of side panels each comprises a second fastening component. The first pair of side panels is folded inwardly over the chassis such that the first fastening components lie between the first and second lateral edges of the chassis, and the second pair of side panels is folded inwardly over the chassis such that the second fastening components lie between the first and second lateral edges of the chassis. The method further includes refastenably engaging the first fastening components and second fastening components while the first fastening components and second fastening components lie between the first and second lateral edges of the chassis.

In some embodiments, the method further includes transporting the refastenable training pant in a machine direction to a folding device. The refastenable training pant may be transported to the folding device with the first pair of side panels are folded inwardly over the chassis such that the first fastening components lie between the first and second lateral edges of the chassis, and the second pair of side panels are folded inwardly over the chassis such that the second fastening components lie between the first and second lateral edges of the chassis. In certain embodiments, the method further includes folding the refastenable training pant about a transverse fold line with the folding device such that the first fastening components of the first pair of side panels face the second fastening components of the second pair of side panels between the first and second lateral edges of the chassis.

In some embodiments, the method may further include folding each of the first pair of side panels inwardly over the chassis such that a first folded portion of each of the first side panels and the first fastening components lie between the first and second lateral edges of the chassis. In some embodiments, the method may include detachably securing the first folded portion of each of the first pair of side panels to the chassis between the first and second lateral edges of the chassis. In certain embodiments, the method may include forming a first breakable bond between the first folded portion of each of the first pair of side panels and the chassis between the first and second lateral edges of the chassis. In other embodiments, the method may include detachably securing the first folded portions to the chassis using respective pockets 180 formed between the chassis 112 and the leg cuffs 121.

In certain embodiments, the method may further include folding each of the second pair of side panels inwardly over the chassis such that a second folded portion of each of the second side panels lies between the first and second lateral edges of the chassis. In such embodiments, a second breakable bond may be formed between the second folded portion of each of the second pair of side panels and the chassis between the first and second lateral edges of the chassis. In certain embodiments, the method may further include folding each of the second pair of side panels outwardly over the second folded portion of each side panels such that a third folded portion of each of the second pair of side panels lies between the first and second lateral edges of the chassis. In such embodiments, at least a third breakable bond may be formed between the third folded portion of each of the second pair of side panels and the chassis between the first and second lateral edges of the chassis. In some embodiments, a fourth breakable bond may be formed between the third folded portion of each of the second pair of side panels and the chassis between the first and second lateral edges of the chassis.

In still other embodiments, a third breakable bond may be formed between the third folded portion of each of the second side panels and the respective second folded portion of each of the second side panels between the first and second lateral edges of the chassis.

In some embodiments, the method may include detachably securing the second and third folded portions of each of the second pair of side panels to the chassis between the first and second lateral edges of the chassis. In embodiments, the method may include detachably securing the second and third folded portions to the chassis using respective pockets 180 formed between the topsheet 116 and the leg cuffs 121.

In some embodiments, the refastenable training pant may be formed by a method which includes: providing a topsheet for forming a portion of a pant chassis; applying a pair of first side panels to the topsheet, each of the pair of first side panels having a refastenable fastening element; folding each of the first side panels to form first folded portions (for example, by folding the first folded portions over the topsheet); and detachably securing the first folded portion of each of the first side panels to the pant chassis. As used herein, the terms "chassis" and "pant chassis" are equivalent.

In an exemplary embodiment, the topsheet may be provided in a form of a continuous web, and the first side panels may be applied to the topsheet, folded, and the first breakable bonds may be formed while the topsheet is in the form of the continuous web. The topsheet has a first and a second lateral edge and the first breakable bonds may be formed between the first and second lateral edges of the topsheet.

In another exemplary embodiment, the topsheet may be provided in the form of a continuous web, the first side panels may be applied to the topsheet, folded, and at least partially inserted into respective pockets 180 formed between the chassis and the leg cuffs 121.

In some embodiments, the method of forming the refastenable training pant may further include affixing a pair of second side panels to the topsheet. The second side panels may be folded to form third folded portions. The second side panels may be folded over the topsheet to form second folded portions. Second breakable bonds may be formed between the second folded portions and the topsheet. Third and fourth breakable bonds may be formed between the third folded portions and the topsheet. In some embodiments, a third breakable bond may instead be formed between the third folded portions and the second folded portions.

In other embodiments, the method of forming the refastenable training pant may further include affixing a pair of second side panels to the topsheet. The second side panels may be folded to form third folded portions. The second side panels may be folded over the topsheet to form second folded portions. The second and third folded portions of the second side panels may each be at least partially inserted into respective pockets 180 formed between the chassis and the leg cuffs 121.

In some embodiments, the method may further include providing a continuous web material forming a backsheet which may be superposed and fixed to the topsheet and the first and second side panels.

Figure 12:
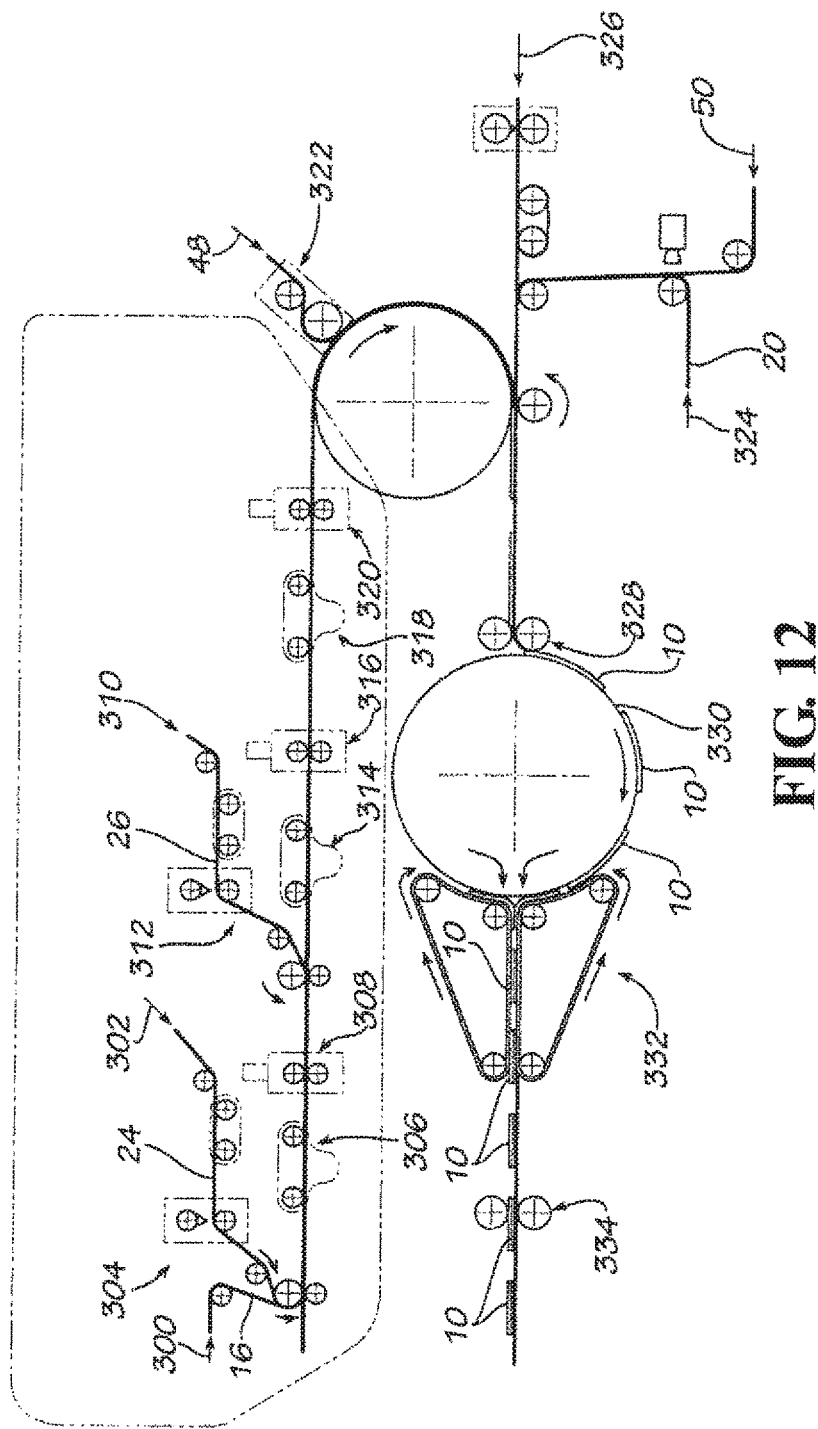
FIG. 12 is a schematic representation of a method for manufacturing a refastenable article in accordance with one or more embodiments of the present disclosure.

FIG. 12 is a schematic example of a process adapted for producing training pants as exemplified in FIGS. 1-5. In this example, the first side panels may be attached to the chassis before the second side panels are attached to the chassis. It should be noted, however, that the first side panels may be attached to the chassis either before or after the second side panels are attached to the chassis.

In the representation of FIG. 12, reference number 300 denotes the source of a continuous web material forming the topsheet 16. The reference number 302 indicates the source of continuous web materials forming the front side panels 24. The front side panels 24 may include the respective fastening elements 44 of the refastenable fastening system 40. In a first side panel attachment device 304, the front side panels 24 may be cut and then applied on the topsheet 16. For example, the front side panels 24 may be bonded to the topsheet 16 with thermal or ultrasonic bonding or the like.

In a first side panel folding device 306, the front side panels 24 may be folded over the topsheet 16 to form the first folded portions 24*a*. As used herein, the terms "folding unit," "side panel folding device," and "folding device" are equivalent. In a first securing device 308, the first breakable bonds 30 may be formed. In some embodiments, the first securing device 308 may be a breakable bond forming device. In embodiments in which the breakable connect is formed by thermal or ultrasonic bonding, a thermal or ultrasonic bonding device may be employed to form a thermal or ultrasonic bond to form the first breakable bonds 30. Alternatively, the breakable connect may be formed with an adhesive. When an adhesive is used, the adhesive may be applied before folding the front side panels 24.

The reference number 310 indicates the source of at least one continuous web material forming the back side panels 26. The back side panels 26 may include the respective fastening elements 42 of the refastenable fastening system 40. In a second side panel attachment device 312 the back side panels 26 may be cut and then applied on the topsheet 16. In a second side panel folding device 314 the back side panels 26 may be folded over topsheet 16 to form the second folded portions 26*a*. In a second securing device 316 the second breakable bonds 36 may be formed. In embodiments in which the breakable connect is formed by thermal or ultrasonic bonding, a thermal or ultrasonic bonding device may be employed to form a thermal or ultrasonic bond to form the second breakable bonds 36. Alternatively, the breakable connect may be formed with an adhesive. When an adhesive is used, the adhesive may be applied before folding the back side panels 26.

In a third side panel folding device 318, the back side panels may be folded over along a third folding line to form the third folded portions 26*b*. In a third securing device 320, the third and fourth breakable bonds 38, 39 may be formed. In embodiments in which the breakable connect is formed by thermal or ultrasonic bonding, a thermal or ultrasonic bonding device may be employed to form a thermal or ultrasonic bond to form the third and fourth breakable bonds 38, 39. Alternatively, the breakable connect may be formed with an adhesive. When an adhesive is used, the adhesive may be applied before folding the back side panels 26. In still other embodiments, the third securing device 320 may be used to make a third breakable bond between the third folded portion of each of the second side panels and the respective second folded portion of each of the second side panels between the first and second lateral edges of the chassis.

An elastic web band attachment unit 322 may apply elastic waist bands 48 to the topsheet 16.

The reference number 324 denotes the source of a continuous web material forming the backsheet 20. Elastic leg members 50 may be applied on the backsheet 20. Absorbent cores 22 coming from a source 326 may then applied to the backsheet 20.

The topsheet 16 with the front and back side panels 24, 26 and elastic waist bands 48 may then be superposed and fixed to the backsheet 20 with the elastic leg members 50 and absorbent cores 22.

A cutting station 328 cuts transversally the continuous webs to form blanks of refastenable articles 10 which are maintained by vacuum on the outer surface of a roller 330.

A folder 332 folds the refastenable articles 10 along respective transverse folding line A. In some embodiments, the folder 332 may maintain the refastenable articles 10 in position during folding by vacuum. For example, the folder 332 may include vacuum nip rolls and/or vacuum conveyors. In other embodiments, the folder 332 may fold the refastenable articles 10 without the assistance of vacuum. Advantageously, it has been found that commercial production speeds may be achieved without the use of vacuum because of the stability provided by the breakable bonds to the side panels and the placement of the folded portions 24a, 26a, and 26b of the side panels 24 and 26 inwardly with respect to the outer perimeter of the chassis 12.

When folding the refastenable article 10 in the folder 332, the refastening elements 42, 44 of the refastenable fastening system 40 and the front and back side panels 24, 26 may be maintained within the chassis between the folded portions 24a, 26a, and 26b and the lateral edges 14 by the breakable bonds.

In some embodiments, the transversal folding operation performed in the folder 332 may bring the hook and loop fastening elements 42, 44 of the refastenable fastening system 40 into contact with each other. In other embodiments, the transversal folding operation performed by the folder 332 may be performed while maintaining separation between the hook and loop fastening elements 42, 44, e.g., with the assistance of vacuum. The hook and loop elements may be connected to each other by pressure rollers 334 to form the final refastenable articles 10. The refastenable articles 10 may thus be closed to the "pre-fastened" condition in which the refastenable article 10 may be packaged and sold.

In some embodiments, a method for making back side panels 26 is provided. FIG. 13 is a schematic example of a method for producing back side panels 26.

In the representation of FIG. 13, reference number 240 denotes the source of a continuous web material 241 forming the back side panels 26. The side panel continuous web material 241 may extend between two longitudinal side edges 262 and has a length substantially parallel to the longitudinal edges. At a cutting unit 243, at least a portion 245 of the web material 241 forming the back side panels 26 may be cut from the continuous web at a repeating interval. In some embodiments, the repeating interval may be determined based on the desired size of the back side panels 26. In some embodiments, the at least a portion 245 of the web material 241 may be cut from a medial region between the two side edges 262. As used herein, the term "medial region" means an area that is centrally located between the two side edges 262.

The reference number 248 indicates the source of a continuous web material forming a loop material 250. The loop material 250 may be applied along the length of the back side panel continuous web material 241 between the longitudinal edges 262 of the back side panel continuous web material in the medial region between the two longitudinal edges. A joining roller 246 may be used to combine the side panel continuous web material 241 with the continuous web material of the loop material 250 and the web materials may be bonded together using a bonding unit 254. Bonding may be accomplished by any means known to those of ordinary skill in the art, including but not limited to ultrasonic bonding. Finally, the combined web materials may pass through a slitter unit 256 that cuts the combined web materials along the length of the side panel continuous web material 241 near the center of the combined side panel continuous web material 241 and continuous web of the loop material 250 between the two side edges 262. In some embodiments, the combined web materials may further be cut into individual pairs of back side panels 26 by cutting across the combined side panel continuous web material 241 and continuous web of the loop material 250 transversely to the length of the side panel continuous web material 241 in the region where the at least a portion 245 of web material forming the back side panels has been cut from the continuous web.

Figure 14A:
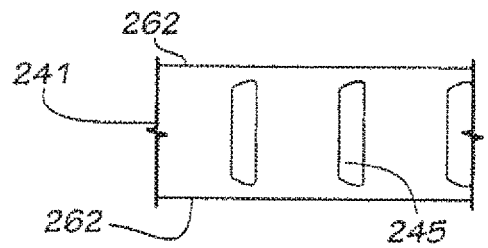
FIG. 14a is a plan view showing the production of back side panels in accordance with one or more embodiments of the present disclosure.

As illustrated in FIG. 14a, at least a portion of the web material forming the back side panels may be cut from the continuous web at a repeating interval. In some embodiments, the cut portion 245 may be in the shape of a trapezoid. In other embodiments, the cut portion 245 may be in the shape of a rectangle or square.

Figure 14B:
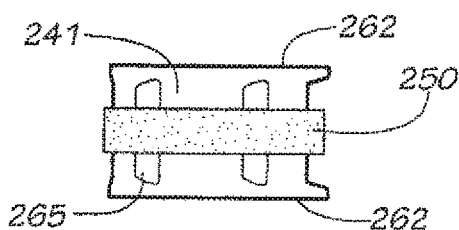
FIG. 14b is a plan view showing the production of back side panels in accordance with one or more embodiments of the present disclosure.

In the representation of FIG. 14b, the band of loop material 250 is shown as may be applied to the web material 241 forming the back side panels 26. In the embodiment illustrated in FIG. 14b, the band of loop material 250 may be applied between the two side edges 262. In some embodiments, the band of loop material 250 may be applied medially between the two side edges 262.

Figure 14C:
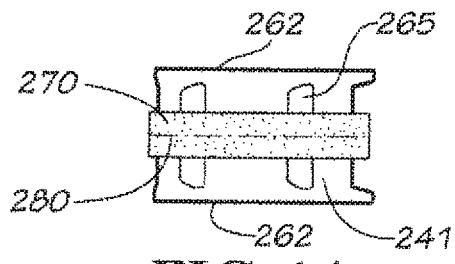
FIG. 14c is a plan view showing the production of back side panels in accordance with one or more embodiments of the present disclosure.

In the representation of FIG. 14c, and in some embodiments, the combined web materials are shown as being cut at the center between of the two side edges 262. In some embodiments, the combined web materials may further be cut into individual pairs of back side panels 26 by separating in the region where the at least a portion of web material forming the back side panels, the cut portion 245, has been cut from the back side panel continuous web material 241.

Figure 14D:
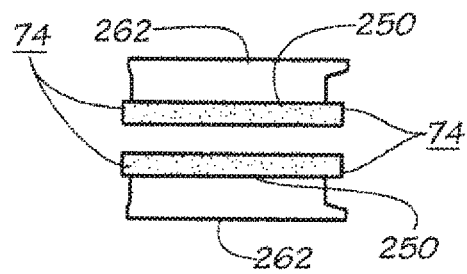
FIG. 14d is a plan view showing the production of back side panels in accordance with one or more embodiments of the present disclosure.

As shown in FIG. 14d, the cut back side panels 26 may include the tabbed portions 74 described hereinabove. In some embodiments, these tabbed portions may be formed by the continuous web of the loop material 250.

In some embodiments, the sequence of steps illustrated by FIGS. 13 and 14a-14d may be performed in an offline process. In other embodiments, the combined side panel continuous web material 241 and continuous web of the loop material 250 illustrated in FIG. 14c may be slit longitudinally with the slitter unit 256 as described above and then fed into the refastenable article production process as the source of continuous web materials 102 forming the back side panels 26 that may be individually cut and then attached to the topsheet 16. This training pant production process is illustrated in FIG. 12.

Figure 15:
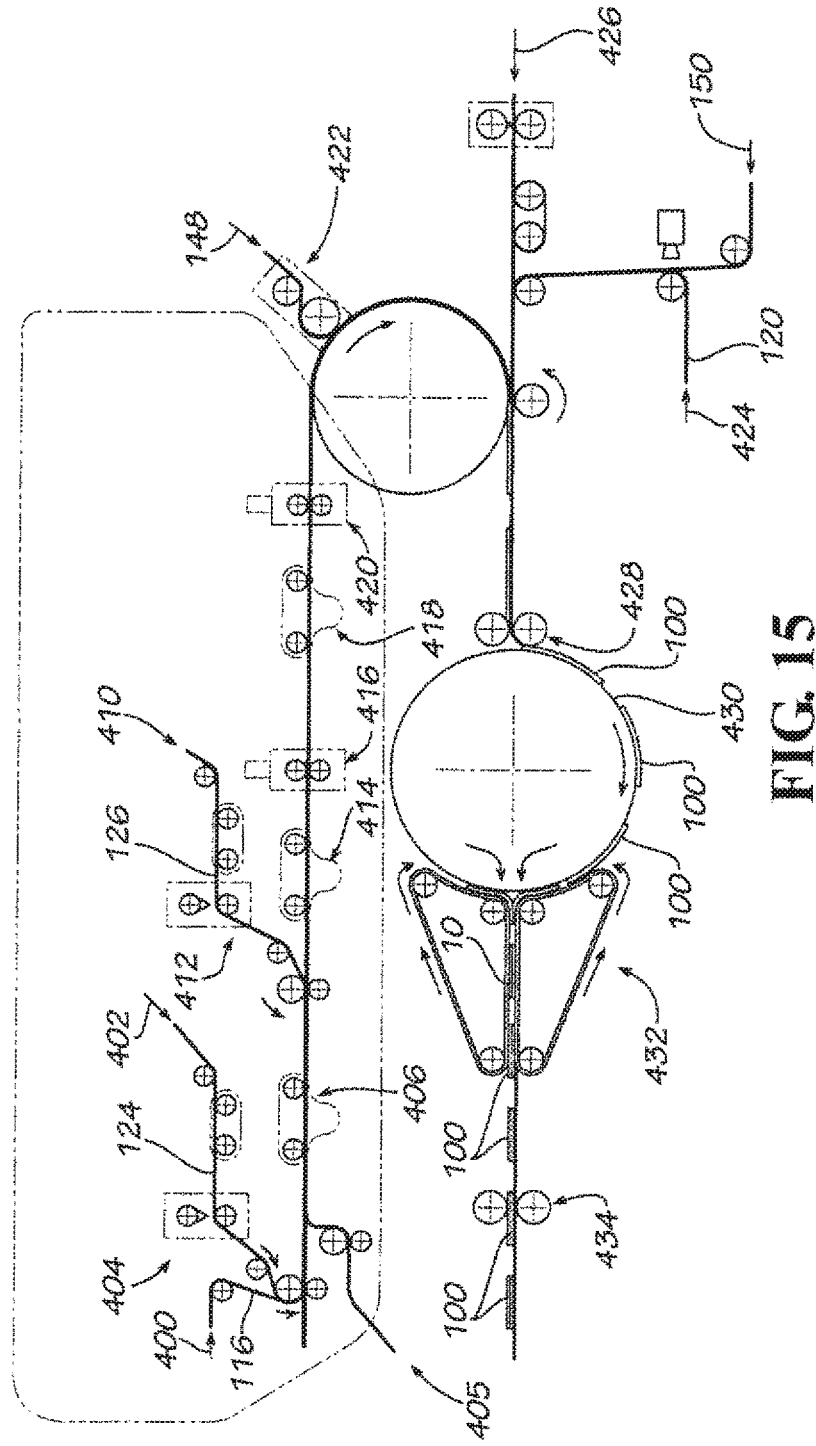
FIG. 15 is a schematic representation of a method for manufacturing a refastenable article in accordance with one or more embodiments of the present disclosure.

FIG. 15 is a schematic example of a process adapted for producing training pants as exemplified in FIGS. 6-9.

In the representation of FIG. 15, reference number 400 denotes the source of a continuous web material forming the topsheet 116. The reference number 402 indicates the source of continuous web materials forming the front side panels 124. The front side panels 124 may include the respective fastening elements 144 of the refastenable fastening system 140. In a first side panel attachment device 404, the front side panels 124 may be cut and then may be applied on the topsheet 116. For example, the front side panels 124 may be bonded to the topsheet 116 with thermal or ultrasonic bonding or the like.

A leg cuff attachment unit 405 may be provided for attaching the leg cuffs 121 to the topsheet 116. The leg cuff attachment unit 405 may attach the leg cuffs 121 to the topsheet 116 with an adhesive or by thermal or ultrasonic bonding. The leg cuffs 121 may be configured to create pockets 180 adjacent to the corners of the topsheet 116. The pockets 180 may be used to at least partially secure the folded front and back side panels 124, 126 such that the transversal folding operation performed in the folder 432 will bring the hook and loop fastening elements 142, 144 of the refastenable fastening system 140 into contact with each other.

In a first side panel folding device 406, the front side panels 124 may be folded over the topsheet 116 to form the first folded portions 124a. In a first securing device 416, the folded front side panels 124 may be at least partially inserted (i.e., tucked) into respective pockets 180 that may be located adjacent to one of the first and second lateral edges of the chassis. In some embodiments, the first securing device 416 may comprise a tucking device. In some embodiments, the first securing device 416 may at least partially insert the folded front side panels 124 into respective pockets 180 that are formed between the leg cuffs 121 and the topsheet 118 of the chassis 116.

The reference number 410 indicates the source of at least one continuous web material forming the back side panels 126. The back side panels 126 may include the respective fastening elements 142 of the refastenable fastening system 140. In a second side panel attachment device 412 the back side panels 126 may be cut and then applied on the topsheet 116. In a second side panel folding device 414 the back side panels 126 may be folded over topsheet 116 to form the second folded portions 126a. In a third side panel folding device 418 the back side panels 126 may again be folded over to form the second folded portions 126b.

In a second securing device 420 the folded back side panels 126 may be at least partially inserted (i.e., tucked) into respective pockets 180 that may be located adjacent to one of the first and second lateral edges of the chassis 116. In some embodiments, the second securing device 420 may at least partially insert the folded back side panels 126 into respective pockets 180 that may be formed between the leg cuffs 121 and the topsheet 118 of the chassis 116.

An elastic web band attachment unit 422 may apply elastic web bands 148 to the topsheet 116.

The reference number 424 denotes the source of a continuous web material forming the backsheet 120. Elastic leg members 150 may be applied on the backsheet 120. Absorbent cores 122 coming from a source 426 may then be applied to the backsheet 120.

The topsheet 116 with the front and back side panels 124, 126 and elastic waist band 148 may then be superposed and fixed to the backsheet 120 with the elastic leg members 150 and absorbent cores 122.

A cutting station 428 cuts transversally the continuous webs to form blanks of refastenable articles 100 which may be maintained by vacuum on the outer surface of a roller 430.

A folder 432 may fold the refastenable articles 100 along respective transverse folding line A. In some embodiments, the folder 432 may maintain the refastenable articles 100 in position during folding by vacuum. For example, the folder 432 may include vacuum nip rolls and/or vacuum conveyors. In other embodiments, the folder 432 may fold the refastenable articles 100 without the assistance of vacuum.

When folding the refastenable article 100 in the folder 432, the refastening elements 142, 144 of the refastenable fastening system 140 and the front and back side panels 124, 126 may be maintained between the folded portions 124a, 126a, and 126b and the lateral edges 114 by the means of detachable securement, for instance a pocket 180.

In some embodiments, the transversal folding operation performed in the folder 432 may bring the hook and loop fastening elements 142, 144 of the refastenable fastening system 140 into contact with each other. In other embodiments, the transversal folding operation performed by the folder 432 may be performed while maintaining separation between the hook and loop fastening elements 142, 144, e.g., with the assistance of vacuum. The hook and loop elements are connected to each other by pressure rollers 434 to form the final refastenable articles 100. The refastenable articles 100 are thus closed to the "pre-fastened" condition in which the refastenable article 100 is packaged and sold.

Apparatus for Manufacturing Refastenable Training Pants

Apparatuses for manufacturing a refastenable article are also disclosed. In one aspect, the apparatus has a first side panel attachment device adapted to attach a first side panel having a first refastenable fastening element to the first lateral edge of a pant chassis. The apparatus includes a first side panel folding device adapted to receive the first side panel and to fold the first side panel in a direction substantially transverse to a lateral edge of the pant chassis to form a first folded portion. When attached to the pant chassis, the first folded portion is folded inwardly over the pant chassis and extends between the first and second lateral edges of the pant chassis. The apparatus further includes a securing device adapted to secure the first folded portion of the first side panel to the pant chassis.

In some embodiments, the apparatus may include a first transport device for transporting the pant chassis to the first side panel attachment device. The first transport device may be adapted to transport the pant chassis as a continuous web of topsheet material.

In some embodiments, the apparatus may include a second side panel attachment device that may be adapted to attach a second side panel having a second refastenable fastening element to the pant chassis adjacent to the first lateral edge of the pant chassis. The apparatus may also include a second side panel folding device that is adapted to receive the second side panel and to fold the second side panel in a second direction substantially transverse to a second lateral edge of the pant chassis to form a second folded portion. When attached to the pant chassis, the second folded portion may be folded inwardly over the pant chassis and extend between the first and second lateral edges of the pant chassis. In certain embodiments, the apparatus may further include a second breakable bond forming device that is adapted to form a second breakable bond 36 between the second folded portion of the second side panel and the pant chassis.

In some embodiments, the apparatus may include a third side panel folding device adapted to receive the second side panel and fold the side panel in a third direction substantially transverse to the second waist edge to form a third folded portion, wherein the third folded portion may be folded outwardly over the second folded portion.

In some embodiments, the apparatus may further include a third breakable bond forming device that may be adapted to form a third breakable bond 38 between the third folded portion of the second side panel and the pant chassis. In some embodiments, the apparatus may also include a fourth breakable bond forming device that may be adapted to form a fourth breakable bond 39 between the third folded portion of the second side panel and the pant chassis. In some embodiments, the third breakable 38 bond may be formed between a first tabbed portion 74 of the third folded portion of each of the second pair of side panels and the pant chassis, where the first tabbed portion 74 extends from one of a trailing edge or a leading edge of a distal region of the third folded portion. In some embodiments, the fourth breakable bond 39 may be formed between a second tabbed portion 74 of the third folded portion of each of the second pair of side panels and the pant chassis, where the second tabbed portion 74 extends from another of a trailing edge or a leading edge of the distal region of the third folded portion.

In still other embodiments, a third breakable bond forming device may be adapted to form a third breakable bond between the third folded portion of each of the second side panels and the respective second folded portion of each of the second side panels between the first and second lateral edges of the pant chassis.

In some embodiments, the apparatus may further include a second transport device adapted to transport a continuous web of backsheet material to join with the continuous web of topsheet material after the continuous web of topsheet of material has the first and the second side panels affixed thereto. The apparatus may also include an attachment device for fixing the continuous web of backsheet material to the continuous web of topsheet material.

The apparatus may include a bifolder device that is configured to fold the pant chassis, the first side panels, and the second side panels about a central fold line substantially parallel to the first and second waist edges such that the first refastenable fastening elements and second refastenable fastening elements face each other between the first and second lateral edges of the pant chassis. In certain embodiments, the apparatus may further include a fastening station that is configured to compress the pant chassis and thereby refastenably engage the first and second refastenable fastening elements while the refastenable fastening elements are between the first and second lateral edges of the pant chassis.

In another aspect, an apparatus is provided for preparing a refastenable training pant for packaging. The apparatus may include a pant assembly system configured to prepare a refastenable training pant that includes a chassis having a leading edge, a trailing edge, and first and second lateral edges extending in a longitudinal direction between the leading edge and the trailing edge. The refastenable training pant may also include a first pair of side panels attached to the chassis proximal to one of the leading edge and the trailing edge of the chassis and a second pair of side panels attached to the chassis proximal to another of the leading edge and the trailing edge of the chassis. The first pair of side panels may each include a first fastening component and the second pair of side panels may each include a second fastening component. The first pair of side panels may be folded inwardly over the chassis such that the first fastening components lie between the first and second lateral edges of the chassis, and the second pair of side panels may also be folded inwardly over the chassis such that the second fastening components lie between the first and second lateral edges of the chassis. The apparatus may also include a pant transport device that may be adapted to transport the refastenable training pant in a machine direction while the first and second fastening components lay between the first and second lateral edges of the chassis in an unfastened state. The apparatus may further include a fastening station that may be adapted to refastenably engage the first fastening components and second fastening components while the first fastening components and second fastening components lay between the first and second lateral edges of the chassis.

In some embodiments, the apparatus may further include a folding device that may be adapted to fold the refastenable training pant about a transverse fold line such that the first fastening components of the first pair of side panels face the second fastening components of the second pair of side panels between the first and second lateral edges of the chassis.

The apparatus may also include a first side panel attachment device adapted to attach the first pair of side panels to the first and second lateral edges of the chassis. In certain embodiments, the apparatus may further include a first side panel folding device that may be adapted to receive the first pair of side panels and fold each of the first pair of side panels substantially transverse to a lateral edge of the chassis to form a first folded portion. When attached to the chassis, the first folded portion may be folded inwardly over the chassis and extend between the first and second lateral edges of the chassis. The apparatus may also include a breakable bond forming device that is adapted to form a breakable bond between the first folded portions of the first side panels and the chassis.

In some embodiments, the apparatus may also include a second transport device for transporting the chassis to the second side panel attachment device. For example, the second transport device may be adapted to transport the chassis as a continuous web of topsheet material. The apparatus may further include a second side panel attachment device that is adapted to attach the second pair of side panels to the first and second lateral edges of the chassis. The apparatus may also include a second side panel folding device adapted to receive the second pair of side panels and to fold each of the second pair of side panels substantially transverse to a second waist edge to form a second folded portion, wherein when attached to the chassis the second folded portion is folded inwardly over the chassis and extends between the first and second lateral edges of the chassis. In certain embodiments, the apparatus may further include a second breakable bond forming device that may be adapted to form a second breakable bond 36 between the second folded portions of the second side panels and the chassis.

In some embodiments, the apparatus may further include a third side panel folding device adapted to receive the second pair of side panels and fold each of the second pair of side panels substantially transverse to the second waist edge to form a third folded portion, wherein when attached to the chassis the third folded portion may be folded outwardly over the second folded portion. The apparatus may also include a third breakable bond forming device adapted to form a third breakable bond 38 between the third folded portion of each of the second pair of side panels and the chassis. In some embodiments, the apparatus may also include a fourth breakable bond forming device that may be adapted to form a fourth breakable bond 39 between the third folded portion of the second side panel and the chassis. In some embodiments, the third breakable bond 38 may be formed between a first tabbed portion 74 of the third folded portion of each of the second pair of side panels and the chassis, where the first tabbed portion 74 extends from one of a trailing edge or a leading edge of a distal region of the third folded portion. In some embodiments, the fourth breakable bond 39 may be formed between a second tabbed portion 74 of the third folded portion of each of the second pair of side panels and the chassis, where the second tabbed portion 74 extends from another of a trailing edge or a leading edge of the distal region of the third folded portion.

In still other embodiments, a third breakable bond may be formed between the third folded portion of each of the second side panels and the respective second folded portion of each of the second side panels between the first and second lateral edges of the chassis.

In certain embodiments, the apparatus may include a third transport device that may be adapted to transport a continuous web of backsheet material to join with the continuous web of topsheet material after the continuous web of topsheet of material has the first and the second side panels affixed thereto. In such embodiments, the apparatus may further include an attachment device for fixing the continuous web of backsheet material to the continuous web of topsheet material.

FIG. 12 schematically illustrates an apparatus that is adapted for producing training pants as exemplified in FIG. 3. In this example, the front side panels are attached to the chassis before the back side panels are attached to the chassis. It should be noted, however, that the back side panels may be attached to the chassis either before or after the front side panels are attached to the chassis.

A first side panel attachment device 304 is provided for attaching the front side panels 24 to the pant chassis. The front side panels 24 may be fed to the first side panel attachment device 304 as continuous web materials 302. (An embodiment of an apparatus for making the side panels 26 is illustrated in FIG. 13 which is described in detail hereinabove.) The continuous web materials 302 may include the fastening element 44 of the refastenable fastening system 40. The front side panels 24 may then be cut from the continuous web material 302 and then may be applied on the topsheet 16, which may be fed to the first side panel attachment device 304 as a continuous web material 300. The first side panel attachment device 304 may function to permanently bond the front side panels 24 to the topsheet 16. For example, the first side panel attachment device 304 may include an adhesive application device for applying a permanent adhesive to the topsheet 16 and/or front side panels 24 or may include a device for thermally or ultrasonically bonding the front side panels 24 to the topsheet 16.

A first side panel folding device 306 may be provided for folding the front side panels 24 over topsheet 16 to form the first folded portions 24a. The first side panel folding device 306 may include, for example, a folding board or a folding conveyor. The first side panel folding device 306 may be positioned upstream or downstream relative to the second side panel attachment device 312 or the first side panel folding device 306 may be incorporated into the first side panel attachment device 304.

A first securing device 308 may be provided for forming the first breakable bonds 30. In some embodiments, the first securing device 308 may be a breakable bond forming device. In embodiments in which the breakable bond is formed by thermal or ultrasonic bonding, a thermal or ultrasonic bonding device may be employed to form a thermal or ultrasonic bond to form the first breakable bonds 30. In embodiments where an adhesive is used to form the first breakable bonds 30, the first securing device 308 may be located upstream of the first side panel folding device 306.

A second side panel attachment device 312 may be provided for attaching the back side panels 26 to the pant chassis. The back side panels 26 may be fed to the second side panel attachment device 312 as two continuous web materials 310. The continuous web materials 310 may include the fastening element 42 of the refastenable fastening system 40. The back side panels 26 may then cut from the continuous web material 310 and then applied on the topsheet 16, which may be fed to the second side panel attachment device 312 as a continuous web material 310. The second side panel attachment device 312 may include a device for permanently bonding the back side panels 26 to the topsheet 16. For example, the side panel attachment device 312 may include an adhesive application device for applying a permanent adhesive to the topsheet 16 and/or back side panels 26 or may include a device for thermally or ultrasonically bonding the back side panels 26 to the topsheet 16.

A second side panel folding device 314 may be provided for folding the back side panels 24 over the topsheet 16 to form the second folded portions 26a. The second side panel folding device 314 may include, for example, a folding board or a folding conveyor. The second side panel folding device 314 may be positioned upstream or downstream relative to the first side panel attachment device 304 or the first side panel folding device 306 may be incorporated into the first side panel attachment device 304.

A second securing device 316 may be provided for forming the second breakable bonds 36. In embodiments in which the breakable bond is formed by thermal or ultrasonic bonding, a thermal or ultrasonic bonding device may be employed to form a thermal or ultrasonic bond to form the second breakable bonds 36. In embodiments where an adhesive is used to form the second breakable bonds 36, the second securing device 316 may be located upstream of the second side panel folding device 314.

A third side panel folding device 318 may be provided for folding the back side panels 26 along the third folding line 34 to form the third folded portions 26b. The third side panel folding device 318 may include, for example, a folding board or a folding conveyor. The third side panel folding device 318 may be positioned upstream or downstream relative to the first side panel attachment device 304 or the third side panel folding device 318 may be incorporated into the first side panel attachment device 304.

A third securing device 320 may be provided for forming the third and fourth breakable bonds 38, 39. In some embodiments, separate securing devices may be provided for forming each of the third breakable bonds 38 and the fourth breakable bonds 39. In embodiments in which the breakable bonds are formed by thermal or ultrasonic bonding, thermal or ultrasonic bonding devices may be employed to form a thermal or ultrasonic bond to form the third and fourth breakable bonds 38, 39. In embodiments where an adhesive is used to form the third and/or fourth breakable bonds 38, 39, the third securing device 320 may be located upstream of the third side panel folding device 318.

An elastic web band attachment unit 322 may be provided for attaching the elastic web bands 48 to the topsheet 16. The elastic web band attachment unit 322 may attach the elastic web bands 48 to the topsheet with an adhesive or by thermal or ultrasonic bonding.

In a separate feed line, the elastic leg members 50 may be joined to the backsheet 20, which may be fed as a continuous web material 324. Absorbent cores 22 from a source 326 may then applied to the backsheet 20. The topsheet 16 (with the front and back side panels 24, 26 and elastic waist band 48) may then be superposed and fixed to the backsheet 20 (with the elastic leg members 50 and absorbent cores 22). The topsheet 16 and backsheet 20 may be fixed together by any process known in the art including adhesive, ultrasonic, or thermal bonding.

In some embodiments, a leg cuff attachment unit may be provided for attaching the leg cuffs 21 to the topsheet 16. The leg cuff attachment unit may attach the leg cuffs 21 to the topsheet 16 with an adhesive or by thermal or ultrasonic bonding.

A cutting station 328 may be provided for transversally cutting the continuous webs to form blanks of refastenable articles 10. The cut refastenable articles 10 may then be fed to a roller 330. The refastenable articles 10 may be maintained on the outer surface of a roller 330 by vacuum.

A folder 332, which may be referred to as a bifolder, folds the refastenable articles 10 along respective transverse folding lines A as the crotch region 29 of the refastenable article 10 may be fed through a folding nip which may include a pair of nip rollers. The roller 330 may include a pusher for ejecting the refastenable article 10 from the folder into the folding nip.

The folder may include a pair of conveyors, for example, top and bottom conveyors in the present illustration, which pull the refastenable article 10 through the folding nip and transport the refastenable article 10 downstream of the folding nip. In some embodiments, the folder 332 may maintain the refastenable articles 10 in position against the conveyors during folding by vacuum. For example, the folder 332 may include vacuum nip rolls at the folding nip and/or vacuum conveyors. In some embodiments, the conveyors may each include a belt with areas for gripping the refastenable articles 10. The gripping areas may be formed by a plurality of seats that are recessed with respect to the outer surfaces of the belts. The gripping areas for picking up refastenable articles 10 are provided with holes for picking up the refastenable articles 10 by vacuum suction. The arrangement of holes may be such as to reproduce the shapes of the respective front half and rear half of the refastenable article 10. The surfaces of the top and bottom belts may be sufficiently close so as to compress between them the side panels 24, 26. This solution enables fastening of the refastenable article 10 directly during the step of folding. Further details about the conveyors may be found in U.S. Provisional Patent Application Ser. No. 61/453,677, filed on Mar. 17, 2011, the contents of which are hereby incorporated by reference in their entirety.

In other embodiments, the folder 332 may fold the refastenable articles 10 without the assistance of vacuum. Advantageously, it has been found that commercial production speeds may be achieved without the use of vacuum because of the stability provided by the breakable bonds to the side panels.

When folding the refastenable article 10 in the folder 332, the refastening elements 42, 44 of the refastenable fastening system 40 and the front and back side panels 24, 26 may be maintained within the chassis between the folded portions 24a, 26a, and 26b and the lateral edges 14 by detachable securement such that the folded portions 24a, 26a, and 26b of the side panels 24 and 26 are disposed inwardly with respect to the outer perimeter of the chassis 12.

In some embodiments, the transversal folding operation performed in the folder 332 may bring the hook and loop fastening elements 42, 44 of the refastenable fastening system 40 into contact with each other. In other embodiments, the transversal folding operation performed by the folder 332 may be performed while maintaining separation between the hook and loop fastening elements 42, 44, e.g., with the assistance of vacuum. The hook and loop elements may be connected to each other by pressure rollers 334 to form the final refastenable articles 10. The refastenable articles 10 may thus be closed to the "pre-fastened" condition in which the refastenable article 10 is packaged and sold.

FIG. 15 schematically illustrates an apparatus that is adapted for producing training pants as exemplified in FIGS. 6-9. In this example, the first side panels are attached to the chassis before the second panels are attached to the chassis. It should be noted, however, that the first side panels may be attached to the chassis either before or after the second side panels are attached to the chassis.

A first side panel attachment device 404 is provided for attaching the front side panels 124 to the pant chassis. The front side panels 124 may be fed to the first side panel attachment device 404 as continuous web materials 402. The continuous web materials 402 may include the fastening element 144 of the refastenable fastening system 140. The front side panels 124 may then be cut from the continuous web material 402 and then may be applied on the topsheet 116, which is fed to the first side panel attachment device 404 as a continuous web material 400. The first side panel attachment device 404 may include a device for permanently bonding the front side panels 124 to the topsheet 116. For example, the first side panel attachment device 404 may include an adhesive application device for applying a permanent adhesive to the topsheet 116 and/or front side panels 124 or may include a device for thermally or ultrasonically bonding the front side panels 124 to the topsheet 116.

A leg cuff attachment unit 405 may be provided for attaching the leg cuffs 121 to the topsheet 116. The leg cuff attachment unit 405 may attach the leg cuffs 121 to the topsheet 116 with an adhesive or by thermal or ultrasonic bonding. The leg cuffs 121 may be configured to create pockets 180 adjacent to the corners of the topsheet 116. The pockets 180 may be used to at least partially secure the folded front and back side panels 124, 126 such that the transversal folding operation performed in the folder 432 will bring the hook and loop fastening elements 142, 144 of the refastenable fastening system 140 into contact with each other.

A first side panel folding device 406 may be provided for folding the front side panels 124 over the topsheet 116 to form the first folded portions 124a. The first side panel folding device 406 may include, for example, a folding board or a folding conveyor. The first side panel folding device 406 may be incorporated into the first side panel attachment device 404.

A first securing device 416 may be provided for at least partially inserting (i.e., tucking) the folded front side panels 124 into respective pockets 180 that may be located adjacent to each of the first and second lateral edges of the chassis. In some embodiments, the first securing device 416 may comprise a tucking device. In some embodiments, the first securing device 416 may at least partially insert the folded front side panels 124 into respective pockets 180 that are formed between the barrier leg cuffs 121 and the topsheet 116.

In still other embodiments, the first side panel folding device 406 may fold the front side panels 124 over the topsheet 116 to form the first folded portions 124a. The leg cuff attachment unit 405 may then attach the leg cuffs 121 to the topsheet 116. The leg cuffs 121 may be configured to create pockets 180 adjacent to the corners of the topsheet 116. The pockets 180 may be used to at least partially secure the folded front side panels 124.

A second side panel attachment device 412 may be provided for attaching the back side panels 126 to the pant chassis. The back side panels 126 may be fed to the second side panel attachment device 412 as two continuous web materials 410. The continuous web materials 410 may include the fastening element 142 of the refastenable fastening system 140. The back side panels 126 may then be cut from the continuous web material 410 and may then applied on the topsheet 116, which may be fed to the second side panel attachment device 412 as a continuous web material 410.

A second side panel folding device 414 may be provided for folding the back side panels 126 over the topsheet 116 to form the second folded portions 126a. The second side panel folding device 414 may include, for example, a folding board or a folding conveyor. The second side panel folding device 414 may be positioned upstream or downstream relative to the first side panel attachment device 404 or the second side panel folding device 414 may be incorporated into the first side panel attachment device 404.

A third side panel folding device 418 may be provided for folding the back side panels 126 along the third folding line 134 to form the third folded portions 126b. The third side panel folding device 418 may include, for example, a folding board or a folding conveyor. The third side panel folding device 418 may be positioned upstream or downstream relative to the first side panel attachment device 404 or the third side panel folding device 418 may be incorporated into the first side panel attachment device 404.

A second securing device 420 may be provided for at least partially inserting (i.e., tucking) the folded back side panels 126 into respective pockets 180 that may be located adjacent to each of the first and second lateral edges of the chassis. In some embodiments, the second securing device 420 may at least partially insert the folded back side panels 126 into respective pockets 180 that are formed between the barrier leg cuffs 121 and the topsheet 116.

In still other embodiments, the first side panel folding device 406 may fold the front side panels 124 over the topsheet 116 to form the first folded portions 124a. The second side panel folding device 414 may be provided for folding the back side panels 126 over the topsheet 116 to form the second folded portions 126a. The third side panel folding device 418 may be provided for folding the back side panels 126 along the third folding line 134 to form the third folded portions 126b. The leg cuff attachment unit 405 may then attach the leg cuffs 121 to the topsheet 116. The leg cuffs 121 may be configured to create pockets 180 adjacent to the corners of the topsheet 116. The pockets 180 may be used to at least partially secure the folded front and back side panels 124, 126.

An elastic web band attachment unit 422 may be provided for attaching the elastic web bands 148 to the topsheet 116. The elastic web band attachment unit 422 may attach the elastic web bands 148 to the topsheet 116 with an adhesive or by thermal or ultrasonic bonding.

In a separate feed line, the elastic leg members 150 may be joined to the backsheet 120, which may be fed as a continuous web material 424. Absorbent cores 122 from a source 426 may then be applied to the backsheet 120. The topsheet 116 (with the front and back side panels 124, 126 and elastic waist band 148) may then be superposed and fixed to the backsheet 120 (with the elastic leg members 150 and absorbent cores 122). The topsheet 116 and backsheet 120 may be fixed together by any process known in the art including adhesive, ultrasonic, or thermal bonding.

A cutting station 428 may be provided for transversally cutting the continuous webs to form blanks of refastenable articles 100. The cut refastenable articles 100 may then be fed to a roller 430. The refastenable articles 10 may be maintained on the outer surface of a roller 430 by vacuum.

A folder 432, which may be referred to as a bifolder, may fold the refastenable articles 100 along respective transverse folding lines A as the crotch region 129 of the refastenable article 100 is fed through a folding nip which includes a pair of nip rollers. The roller 430 may include a pusher for ejecting the refastenable article 100 from the folder into the folding nip. The folder may include a pair of conveyors, for example, top and bottom conveyors in the present illustration, which may pull the refastenable article 100 through the folding nip and transport the refastenable article 100 downstream of the folding nip. In some embodiments, the folder 432 may maintain the refastenable articles 100 in position against the conveyors during folding by vacuum. Additional details of the bifolder are the same as those described hereinabove. For example, the folder 432 may include vacuum nip rolls at the folding nip and/or vacuum conveyors. In other embodiments, the folder 432 may fold the refastenable articles 100 without the assistance of vacuum.

When folding the refastenable article 100 in the folder 432, the refastening elements 142, 144 of the refastenable fastening system 140 and the front and back side panels 124, 126 may be maintained within the chassis between the folded portions 124a, 126a, and 126b and the lateral edges 114 by the respective pockets 180 such that the folded portions 124a, 126a, and 126b of the side panels 124 and 126 are disposed inwardly with respect to the outer perimeter of the chassis 112.

In some embodiments, the transversal folding operation performed in the folder 432 may bring the hook and loop fastening elements 142, 144 of the refastenable fastening system 140 into contact with each other. In other embodiments, the transversal folding operation may be performed by the folder 432 and may be performed while maintaining separation between the hook and loop fastening elements 142, 144, e.g., with the assistance of vacuum. The hook and loop elements may be connected to each other by pressure rollers 434 to form the final refastenable articles 100. The refastenable articles 100 may thus be closed to the "prefastened" condition in which the training pant refastenable article 100 may be packaged and sold.

While adhesively connected elements have been considered by way of example, various embodiments may adopt connection via thermal bonding, ultrasound bonding, gluing, or combinations of the various techniques considered.

Those who are skilled in the art will promptly appreciate that the representations of FIGS. 12 and 15 are by their nature schematic. Other features of the apparatus and system of FIGS. 12 and 15 not specifically considered herein are conventional in the art, thus making it unnecessary to provide detailed description herein.

Of course, without prejudice to the underlining principles of the invention, the details and embodiments may vary, even significantly, with respect to what has been described and illustrated herein merely by way of example, without departing from the scope of the invention as defined by the annexed claims.

We claim:

1. A method of preparing a refastenable training pant comprising:
   providing a topsheet for forming a portion of a pant chassis;
   applying a pair of first side panels to the topsheet, each of the pair of first side panels having a refastenable fastening element;
   affixing a pair of second side panels to the topsheet;
   folding each of the first side panels to form first folded portions; and
   detachably securing the first folded portion of each of the first side panels to the pant chassis.

2. The method of claim 1, wherein the step of detachably securing comprises forming first breakable bonds between the first folded portion of each of the first side panels and the pant chassis.

3. The method of claim 1, further comprising folding the second side panels inwardly over the pant chassis to form second folded portions.

4. The method of claim 3, further comprising folding each of the second pair of side panels outwardly over the pant chassis such that a third folded portion is formed.

5. The method of claim 4, further comprising forming a second breakable bond between the second folded portions and the topsheet, and forming at least a third breakable bond between the third folded portions and the topsheet.

6. The method of claim 5, wherein the at least a third breakable bond is formed between a first tabbed portion of the third folded portions and the topsheet, the first tabbed portion extending from a trailing edge or a leading edge of a distal region of the third folded portions.

7. The method of claim 6, further comprising a method for making a pair of second side panels, the method comprising:
   providing a continuous web material comprising two longitudinal side edges;
   cutting at least a portion of the web material from the continuous web material at a repeating interval, wherein the at least a portion of the web material is cut from a medial region between the two longitudinal side edges;
   bonding a loop material to the web material; and
   dividing the web material and the loop material into a pair of second side panels, wherein the web material is cut at the repeating interval and the loop material forms the first tabbed portion.

8. The method of claim 6, further comprising forming at least a fourth breakable bond between the third folded portion of each of the second pair of side panels and the pant chassis between the first and second lateral edges of the pant chassis.

9. The method of claim 8, wherein the at least a third breakable bond is formed between a first tabbed portion of the third folded portion of each of the second pair of side panels and the pant chassis, the at least a fourth breakable bond is formed between a second tabbed portion of the third folded portion of each of the second panels and the pant chassis, the first tabbed portion extending from one of a trailing edge and a leading edge of a distal region of the third folded portion and the second tabbed portion extending from another of the trailing edge and the leading edge of the distal region of the third folded portion.

10. The method of claim 1, wherein the step of detachably securing comprises at least partially inserting the first folded portion of each of the first side panels into respective pockets.

11. The method of claim 10, wherein the pockets are formed between a leg cuff and the topsheet.

12. The method of claim 10, further comprising at least partially inserting the second and third folded portions of the second side panels into respective pockets.

13. The method of claim 12, wherein the pockets are formed between a leg cuff and the topsheet.

14. The method of claim 1, further comprising providing a continuous web material forming a backsheet.

15. The method of claim 14, further comprising superposing and fixing at least a portion of the topsheet with the first and second side panels to at least a portion of the backsheet.

16. The method of claim 1, wherein the first folded portions are folded over the topsheet.

17. The method of claim 1, wherein the topsheet is provided in a form of a continuous web, and wherein the first side panels are applied to the topsheet and the first side panels are folded while the topsheet is in the form of the continuous web.

18. The method of claim 1, wherein the topsheet is provided in a form of a continuous web, and wherein the first side panels are applied to the topsheet, the first side panels are folded, and the first breakable bonds are formed while the topsheet is in the form of the continuous web.

19. The method of claim 18, wherein the topsheet has a first and a second lateral edge and the first breakable bonds are formed between the first and second lateral edges of the topsheet.

* * * * *